US010085829B2

(12) United States Patent
Soletti et al.

(10) Patent No.: US 10,085,829 B2
(45) Date of Patent: Oct. 2, 2018

(54) APPARATUS FOR CREATING GRAFT DEVICES

(75) Inventors: Lorenzo Soletti, Pittsburgh, PA (US); Mohammed S. El-Kurdi, Pittsburgh, PA (US); Jon McGrath, Duxbury, MA (US); Liem Vu, Needham, MA (US); J. Christopher Flaherty, Topsfield, MA (US)

(73) Assignee: Neograft Technologies, Inc., Taunton, MA (US)

( * ) Notice: Subject to any disclaimer, the term of this patent is extended or adjusted under 35 U.S.C. 154(b) by 532 days.

(21) Appl. No.: 13/979,243

(22) PCT Filed: Jan. 13, 2012

(86) PCT No.: PCT/US2012/021209
§ 371 (c)(1),
(2), (4) Date: Aug. 6, 2013

(87) PCT Pub. No.: WO2012/097229
PCT Pub. Date: Jul. 19, 2012

(65) Prior Publication Data
US 2013/0317285 A1 Nov. 28, 2013

Related U.S. Application Data

(60) Provisional application No. 61/432,914, filed on Jan. 14, 2011.

(51) Int. Cl.
*A61F 2/06* (2013.01)
*A61L 27/28* (2006.01)
(Continued)

(52) U.S. Cl.
CPC ............ *A61F 2/062* (2013.01); *A61L 27/507* (2013.01); *D01D 5/0084* (2013.01); *D01D 13/02* (2013.01); *D04H 1/728* (2013.01); *D04H 1/76* (2013.01)

(58) Field of Classification Search
CPC .... A61F 2/062; D01D 5/0007; D01D 5/0061; D01D 5/0084; A61L 27/507
See application file for complete search history.

(56) References Cited

U.S. PATENT DOCUMENTS

| 4,323,525 A | 4/1982 | Bornat |
| 4,552,707 A | 11/1985 | How |

(Continued)

FOREIGN PATENT DOCUMENTS

| WO | WO 00/30564 A2 | 6/2000 |
| WO | WO 2006/123340 A2 | 11/2006 |

(Continued)

OTHER PUBLICATIONS

Written Opinion of the International Searching Authority issued by the Korean Intellectual Property Office as the International Searching Authority for International Application No. PCT/US2012/021209, dated Aug. 31, 2012, 5 pages.

(Continued)

*Primary Examiner* — Thaddeus Cox
(74) *Attorney, Agent, or Firm* — Wilson Sonsini Goodrich & Rosati

(57) ABSTRACT

An apparatus is provided for applying a restrictive fiber matrix to a conduit to create a graft device. A rotating assembly rotates the conduit, and a polymer delivery assembly delivers the restrictive fiber matrix. A controller controls the polymer deliver assembly and the rotating assembly.

40 Claims, 6 Drawing Sheets

(51) Int. Cl.
　　A61L 27/50　　(2006.01)
　　D04H 1/728　　(2012.01)
　　D04H 1/76　　(2012.01)
　　D01D 5/00　　(2006.01)
　　D01D 13/02　　(2006.01)

(56) References Cited

U.S. PATENT DOCUMENTS

| | | | |
|---|---|---|---|
| 4,798,606 A | | 1/1989 | Pinchuk |
| 6,030,371 A * | | 2/2000 | Pursley .............. A61M 25/0009 427/195 |
| 6,070,443 A * | | 6/2000 | Sato ........................ B21H 1/12 29/407.09 |
| 6,891,077 B2 | | 5/2005 | Rothwell et al. |
| 7,759,099 B2 | | 7/2010 | Wolf et al. |
| 7,759,120 B2 | | 7/2010 | Wolf et al. |
| 7,922,761 B2 | | 4/2011 | Shalev et al. |
| 7,998,188 B2 | | 8/2011 | Zilla et al. |
| 8,057,537 B2 | | 11/2011 | Zilla et al. |
| 8,172,746 B2 | | 5/2012 | Zilla et al. |
| 8,353,814 B2 | | 1/2013 | Villafana et al. |
| 8,465,691 B1 * | | 6/2013 | Zhou ...................... C01G 19/02 264/639 |
| 2002/0042128 A1 | | 4/2002 | Bowlin et al. |
| 2004/0073294 A1* | | 4/2004 | Diaz ........................ A61F 2/91 623/1.42 |
| 2004/0094873 A1 | | 5/2004 | Dubson et al. |
| 2004/0146546 A1 | | 7/2004 | Gravett et al. |
| 2005/0203636 A1 | | 9/2005 | McFetridge |
| 2005/0224999 A1* | | 10/2005 | Andrady .............. D01D 5/0061 264/10 |
| 2006/0075963 A1* | | 4/2006 | Nieponice ................ A61F 2/062 118/417 |
| 2006/0199265 A1* | | 9/2006 | Wolf ........................ A61F 2/062 435/395 |
| 2006/0240061 A1 | | 10/2006 | Atala et al. |
| 2007/0059335 A1* | | 3/2007 | Wolf ........................ A61F 2/062 424/423 |
| 2007/0269481 A1 | | 11/2007 | Li et al. |
| 2008/0032278 A1* | | 2/2008 | Jones ...................... A61F 2/062 435/1.1 |
| 2008/0208316 A1 | | 8/2008 | Shalev et al. |
| 2008/0208323 A1 | | 8/2008 | El-Kurdi et al. |
| 2009/0088828 A1* | | 4/2009 | Shalev ...................... A61F 2/06 623/1.2 |
| 2009/0253328 A1* | | 10/2009 | Watanabe ............ D01D 5/0038 442/327 |
| 2009/0321997 A1* | | 12/2009 | Reneker .............. D01D 5/0038 264/465 |
| 2010/0040663 A1* | | 2/2010 | McAllister ................ A61F 2/07 424/423 |
| 2010/0092687 A1* | | 4/2010 | Sumida ................ D01D 5/0061 427/472 |
| 2010/0160718 A1 | | 6/2010 | Villafana et al. |
| 2010/0194000 A1* | | 8/2010 | Petras .................. D01D 5/0061 264/484 |
| 2012/0116495 A1 | | 5/2012 | Zilla et al. |
| 2012/0330437 A1* | | 12/2012 | El-Kurdi ................ A61F 2/06 623/23.64 |
| 2013/0011508 A1* | | 1/2013 | Kim ...................... D01D 5/0069 425/174.8 E |
| 2013/0018454 A1* | | 1/2013 | Lelkes ...................... A61F 2/06 623/1.32 |

FOREIGN PATENT DOCUMENTS

| | | | | |
|---|---|---|---|---|
| WO | WO 2006136817 A1 * | 12/2006 | .......... | D01D 5/0092 |
| WO | 2010042721 | 4/2010 | | |
| WO | WO 2011/056705 A2 | 5/2011 | | |
| WO | WO 2011/084559 A2 | 7/2011 | | |
| WO | WO 2012/012407 A2 | 1/2012 | | |
| WO | WO 2012/092138 A2 | 7/2012 | | |

OTHER PUBLICATIONS

Ayres, et al. Modulation of anisotropy in electrospun tissue-engineering scaffolds: Analysis of fiber alignment by the fast Fourier transform. Biomaterials 27 (2006) 5524-5534.
Ben-Gal, et al. Expandable external support device to improve saphenous vein graft patency after CABG. J Cardiothorac Surg 2013;8:122.
Castronuovo, J. The sequence of gene expression in cultured human saphenous vein after injury. (2002) J. Vasc. Surg. 35, 146-151.
Chakrabarty, S. Fibrin solubilizing properties of certain anionic and cationic detergents. Thrombosis research 55.4 (1989): 511-519.
Courtney, et al. Design and analysis of tissue engineering scaffolds that mimic soft tissue mechanical anisotropy. Biomaterials. 2006, 27: 3631-3638.
Deitzel, et al. Controlled deposition of electrospun poly(ethylene oxide) fibers. Polymer. 2001, 42: 8163-8170.
Deitzel, et al. The effect of processing variable on the morphology of electrospun nanofibers and textiles. Polymer 42 (2001): 261-272.
European search report and opinion dated Apr. 26, 2016 for EP Application No. 12734253.
Fingerle. Intimal lesion formation in rat carotid arteries after endothelial denudation in absence of medial injury. (1990) Arteriosclerosis, 10, 1082-1087.
Grote, et al. Mechanical stretch enhances mRNA expression and proenzyme release of matrix metalloproteinase-2 (MMP-2) via NAD(P)H oxidase-derived reactive oxygen species. Circulation Research. 2003;92(11): 80-6.
Hermans, et al. Fibrin: structure and interactions. Seminars in thrombosis and hemostasis. vol. 8. No. 1. 1982.
Izzat, et al. Influence of external stent size on early medial and neointimal thickening in a pig model of saphenous vein bypass grafting. Circulation 1996; 94:1741-5.
Janowski-Bell, et al. Histology of Blood Vessels—www2.victoriacollege.edu/dept/bio/Belltutorials/Histology%20Tutorial/Blood%20Vessels/Histology_of_Blood_Vessels.html.
Jeremy, et al. A bioabsorbable (polyglactin), nonrestrictive, external sheath inhibits porcine saphenous vein graft thickening. J Thorac Cardiovasc Surg. 2004;127(6): 1766-72.
Kohler, et al. The effect of rigid external support on vein graft adaptation to the arterial circulation. J Vasc Surg. 1989;9(2): 277-85.
Levorson, et al. Fabrication and characterization of multiscale electrospun scaffolds for cartilage regeneration. Biomed Mater 2013;8:014103. doi:10.1088/1748-6041/8/1/014103.
Linder, V. Mouse model of arterial injury. (1993) Circ. Res., 73, 792-796.
Manchio, J. Disruption of graft endothelium correlates with early failure after off-pump coronary artery bypass surgery. (2005) Ann. Thor. Surg. 79, 1991-1998.
McManus, et al. Electrospun fibrinogen: feasibility as a tissue engineering scaffold in a rat cell culture model. Journal of Biomedical Materials Research Part A 81.2 (2007): 299-309.
McManus, et al. Mechanical properties of electrospun fibrinogen structures. Acta Biomaterialia 2.1 (2006): 19-28.
Mehta, et al. External stenting reduces long-term medial and neointimal thickening and platelet derived growth factor expression in a pig model of arteriovenous bypass grafting. Nat Med. 1998;4(2): 235-9.
Morton, et al. Electrospun fibrin nanofibers for the use in tissue engineering. Modification of fibrin to improve applications in regenerative medicine (2010): 81.
Mosesson, M. W. Fibrinogen and fibrin structure and functions. Journal of Thrombosis and Haemostasis 3.8 (2005): 1894-1904.
Parsonnet, et al. New stent for support of veins in arterial grafts. Arch Surg. 1963;87: 696702.
Perumcherry, et al. A Novel Method for the Fabrication of Fibrin-Based Electrospun Nanofibrous Scaffold for Tissue-Engineering Applications*. Tissue Engineering Part C: Methods 17.11 (2011): 1121-1130.
Ramos, et al. Histologic fate and endothelial changes of distended and nondistended vein grafts. Ann Surg. 1976;183(3): 205-28.

(56) References Cited

OTHER PUBLICATIONS

Reneker, et al. Electrospinning of Nanofibers from Polymer Solutions and Melts. Adv Appl Mech 2007;41. doi:10.1016/S0065-2156(07)41002-X.

Sell, et al. Cross-linking methods of electrospun fibrinogen scaffolds for tissue engineering applications. Biomedical Materials 3.4 (2008): 045001.

Sepehipour, A. Does a 'no-touch' technique result in better vein patency? (2011) Interact Cardiovasc Thorac Surg., 13, 626-630.

Sreerekha, et al. Fabrication of fibrin based electrospun multiscale composite scaffold for tissue engineering applications. Journal of biomedical nanotechnology 9.5 (2013): 790-800.

Stankus, et al. Fabrication of biodegradable elastomeric scaffolds with sub-micron morphologies. J Biomed Mater Res A. 2004;70(4): 603-14.

Stitzel, et al. Controlled fabrication of a biological vascular substitute. Biomaterials. 2006, 27: 1088-1094.

Stooker, et al. Perivenous application of fibrin glue reduces early injury to the human saphenous vein graft wall in an ex vivo model. European Journal of Cardio-thoracic Surgery. 2002, 21: 212-217.

Traver, et al. New Generation Tissue Sealants and Hemostatic Agents: Innovative Urologic Applications. Reviews in Urology. 2006, 8: 104-111.

Vijayan, et al. Long-term reduction of medial and intimal thickening in porcine saphenous vein grafts with a polyglactin biodegradable external sheath. J Vasc Surg. 2004;40(5): 1011-9.

Wan, et al. Differential, time-dependent effects of perivenous application of fibrin glue on medial thickening in porcine saphenous vein grafts. European Journal of Cardio-thoracic Surgery, 29, (2006): 742-747.

Weisel, et al. Computer modeling of fibrin polymerization kinetics correlated with electron microscopy and turbidity observations: clot structure and assembly are kinetically controlled. Biophysical journal 63.1 (1992): 111.

Weisel, et al. Mechanisms of fibrin polymerization and clinical implications. Blood 121.10 (2013): 1712-1719.

Wnek, et al. Electrospinning of nanofiber fibrinogen structures. Nano Letters 3.2 (2003): 213-216.

Xu, et al. Electrospun Nanofiber Fabrication as Synthetic Extracellular Matrix and Its Potential for Vascular Tissue Engineering. Tissue Engineering, vol. 10, No. 7/8, 2004.

Yu, et al. Electrospinning, Encyclopedia of Polymer Science & Technology (2008) 1-20.

Zilla, et al. Constrictive external nitinol meshes inhibit vein graft intimal hyperplasia in nonhuman primates. The Journal of Thoracic and Cardiovascular Surgery 2008;136:717-725.

Zilla, et al. Utilization of shape memory in external vein-graft meshes allows extreme diameter constriction for suppressing intimal hyperplasia: A non-human primate study. J Vasc Surg 2009;49:1532-42.

* cited by examiner

APPARATUS FOR CREATING GRAFT DEVICES

CROSS-REFERENCE TO RELATED APPLICATION

This application is a National Phase Application of International Application No. PCT/US2012/021209 filed Jan. 13, 2012, which claims benefit of priority to U.S. Provisional Application No. 61/432,914 filed Jan. 14, 2011. The contents of both of these applications are hereby incorporated herein by reference in their entirety.

FIELD OF THE INVENTION

The present invention relates generally to systems, methods, and apparatuses to create graft devices for a mammalian patient. In particular, the systems and methods described here provide apparatuses to apply a restrictive fiber matrix to a conduit, such as a saphenous vein graft.

BACKGROUND OF THE INVENTION

Coronary artery disease, leading to myocardial infarction and ischemia, is a leading cause of morbidity and mortality worldwide. Conventional treatment alternatives consist of percutaneous transluminal angioplasty, stenting, and coronary artery bypass grafting (CABG). CABG can be carried out using either arterial or venous conduits and is an effective and widely used treatment to combat coronary arterial stenosis, with nearly 500,000 procedures being performed annually. In addition there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed arterial vein grafts (AVGs) usually require clinical intervention such as an additional surgery.

IH accounts for 20% to 40% of all AVG failures within the first 5 years. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH may be initiated by the abrupt exposure of the veins to the dynamic mechanical environment of the arterial circulation.

SUMMARY

For the above and other reasons, a need has been identified for devices and methods that can provide enhanced AVGs and other graft devices for mammalian patients. Desirably, the devices will improve long term patency and minimize surgical and device complications. Developing reliable systems and methods to limit (e.g., prevent) the early events of the IH process would contribute to improvements in the outcome of arterial bypass procedures. Therefore, provided herein is a method of mechanically conditioning and otherwise treating and/or modifying an arterial vein graft, or other tubular member such as living tissue or artificial conduits. To this end, provided herein is a method of applying a restrictive fiber matrix to a tubular member to create a graft device. The tubular member is placed in a fiber application device such as an electrospinning unit and a restrictive fiber matrix is applied to surround the tubular member. In some embodiments, the tubular tissue is a vein, such as a saphenous vein, that is used, for instance, in an arterial bypass procedure, such as a coronary artery bypass procedure.

According to some aspects, an apparatus for applying a fiber matrix, such as a restrictive fiber matrix, to a tubular member to create a graft device is disclosed. A rotating assembly can rotate the tubular member, such as at a rate of approximately 250 rpm, and a polymer delivery assembly delivers a fiber matrix to the tubular member. A controller, which can include a user interface, can control the polymer delivery assembly and the rotating assembly.

The apparatus can apply the fiber matrix in a process time under twenty minutes, typically a ten to fifteen minute process that electrospins fibers onto the tubular member. One or more material layers can be applied, prior to, during or after application of the fiber matrix. The apparatus can include a mandrel which is inserted into the tubular member, and a cartridge into which the mandrel is inserted. One or more diagnostic assemblies such as laser micrometers or visualization devices can be included, such as to monitor the fiber application process. The apparatus can be constructed and arranged to apply the fiber matrix in a continuous or varied process. Fiber matrix application can vary along the length of the tubular member or along the thickness of the fiber matrix. In some embodiments, the fiber matrix delivery is changed at the location of an irregularity of the tubular member, such as the location of a sidebranch when the tubular member is a harvested blood vessel.

The tubular member can comprise living tissue, artificial material or both. Living tissue sources can be harvested from the patient receiving the graft device or other mammalian source, and is typically tissue selected from the group consisting of: vein; artery; lymphatic duct; vas deferens; tear duct; intestine; esophagus; ureter; urethra; trachea; bronchi; duct tissue; Eustachian tube; fallopian tube; and combinations of these. Artificial material can comprise various materials such as materials selected from the group consisting of: polytetrafluoroethylene (PTFE); expanded PTFE (ePTFE); polyester; polyvinylidene fluoride/hexafluoropropylene (PVDF-HFP); silicone; polyethylene; polypropylene; polyester based polymer; polyether based polymer; thermoplastic rubber; and combinations of these.

The apparatus can apply a fiber matrix to the tubular member that has properties configured to improve long term patency of the graft device, as well as reduce complications and improve other outcomes. In some embodiments, the fiber matrix comprises an elastic modulus between 0.5 MPa and 1.5 MPa, typically between 0.5 MPa and 1.0 MPa. Fiber matrix thickness is typically greater than 100 µm, more typically greater than 150 µm and even more typically greater than or equal to 220 µm. The fiber matrix can be porous, such as a matrix having a porosity greater than or equal to 80%. The fiber matrix can be permeable to water, such as a matrix having a water permeability greater than or equal to 15 ml/min/cm$^2$ at a pressure of 120 mmHg. The fiber matrix can be constructed and arranged to support circumferential and/or longitudinal wall tensions between 1.0 N/cm and 10.0 N/cm, typically between 2.0 N/cm and 5.0 N/cm. The fiber matrix can comprise a wall elastic tension between 0.8 N/cm and 1.6 N/cm.

The fiber matrix can have a relatively uniform thickness, such as a matrix whose thickness varies less than 25% along the length of the graft device. The fiber matrix can include one or more properties that vary along its length or circumference. Typical properties to be varied include but are not limited to: thickness; fiber size; porosity; nodal points; fiber crystallinity; a mechanical property; and combinations of these. One or more fiber matrix properties can be chosen based on a patient parameter, such as a patient morphological and or functional parameter selected from the group consisting of: vessel size such as inside diameter, outside diameter, length, and/or wall thickness; taper or other geometric property of a harvested vessel or vessel intended for anastomotic attachment; size and location of one or more side branch ostium or antrum within the harvested vessel; patient age or sex; vessel elasticity or compliance; vessel vasculitis; vessel electrical impedance; specific patient genetic factors or traits, specific patient pathologies and combinations of these.

The apparatus controller can include a user interface, such as a graphical interface including user input components and user output components. The graphical interface can be configured to allow input of one or more data used by the apparatus to apply the fiber matrix, such as data selected from the group consisting of: mandrel size; nozzle speed; polymer solution flow rate; process time; and combinations of these. User output components, such as alphanumeric screens, lights such as LEDs, audible transducers such as speakers or buzzers, can provide system status information, such as current system parameter values as well as system warning or alert information. The user input components can include one or more controls configured to perform a function selected from the group consisting of: rotate one or more mandrels; translate one or more nozzles; translate one or more mandrels; rotate one or more nozzles; monitor the environment of an area surrounding the tubular member; maintain the environment of an area surrounding the tubular member such as to maintain pressure, temperature and/or humidity; apply an electrical potential between at least one nozzle and at least one mandrel; and combinations thereof. In some embodiments, the user interface controls the polymer delivery position, such as its axial and/or radial position. In some embodiments, the user interface controller's movement of the tubular member, such as rotational or axial movement of a mandrel inserted into the tubular member, including rotational or axial speed. Alternatively or additionally, in some embodiments, the user interface controls a flow rate of polymer solution delivered to a nozzle of the polymer delivery assembly.

The apparatus can include one or more mandrels, such as one or more mandrels with a length between 30 cm and 35 cm, and outside diameters between 2 mm and 6 mm, typically outside diameters between 2 mm and 4 mm for creation of graft devices for cardiac bypass applications. The apparatus can detect the size of the mandrel, such as when multiple mandrels of different diameters are provided. In some embodiments, the apparatus includes an electrospinning assembly; and the size of the mandrel, automatically detected or entered manually by an operator, can cause one or more fiber application parameters to be adjusted based on the mandrel size. Numerous process parameters, detected automatically or entered manually, can be input into the apparatus such as to configure electrospinning or other fiber matrix application parameters.

The polymer delivery assembly typically delivers a hydrophobic polymer, such as a sterile polymer that has been passed through a 0.2 µm filter. In some embodiments, the polymer delivered comprises polycaprolactone, such as in a solution that is approximately 11.5% weight/volume gr/mL and is delivered to a nozzle at a flow rate between 5 ml/hr and 7 ml/hr. This solution typically comprises a ratio of 1.15 grams of polycaprolactone to 10 ml of a solvent, typically 1,1,1,3,3,3-Hexafluoro-2-propanol. A solvent provided with the polymer typically has a viscosity between 400 cST and 700 cST when measured at a temperature between 20° C. and 22° C., more typically a viscosity between 500 cST and 600 cST when measured at the same temperature. The provided solvent typically has a surface tension that ranges between 21.5 dynes/cm and 22.5 dynes/cm when measured at a temperature between 20° C. and 22° C.

The polymer delivery assembly can be configured to translate axially along the tubular member, such as in a reciprocating or oscillating motion. Alternatively or additionally, the tubular member can be configured to translate, such as when inserted into a mandrel of the apparatus that is secured to a translational motion assembly. The polymer delivery assembly can include one or more nozzles, such as one or more nozzles that are vertically offset from the tubular member prior to, during and/or after electrospinning such that undesired drops of polymer solution that fall from the nozzle due to gravity do not land on a mandrel and/or the tubular member. In some embodiments, the nozzle is approximately 1.5" long with an inner diameter between 0.047" and 0.055". The nozzle can include insulated and non-insulated portions, such as a nozzle with a non-insulated tip at least 1 cm long.

The tubular member is typically positioned less than 20 cm from the tip of a nozzle, usually less than 15 cm and typically approximately 12.5 cm from the nozzle tip. The fiber matrix is applied by sweeping the nozzle over the tubular member, such as with a sweep range that is approximately 10 cm longer than the tubular member itself, such as a nozzle configured to travel up to 5 cm past each end of the tubular member, or at least 1 cm past the end of the tubular member. In some embodiments, the nozzle sweep velocity is approximate 200 mm/sec. Alternatively or additionally, the tubular member can be moved axially relative to a nozzle. In some embodiments, the fiber matrix is applied with an electrospinning process, such as when a +15 kV potential is applied to the nozzle and a −5 kV potential is applied to a mandrel and/or the tubular member. The nozzle can be configured to produce fibers with a diameter between 0.1 µm and 2.0 µm. Multiple nozzles can be included, as well as nozzles with multiple lumens.

The polymer delivery assembly can be further configured to deliver one or more agents to the tubular member, prior to, during, or after the delivery of the polymer solution. Imaging agents can be delivered to image the graft device, such as a radiopaque substance used to image the graft device after implantation into a patient, or a fluorescent agent used to image fibers in flight to the tubular member. A magnetic or paramagnetic material can be delivered, such as to view the device pre or post implantation with magnetic imaging systems commonly found in a hospital setting.

A chamber can surround the tubular member during application of the fiber matrix, such as a chamber insulated with activated carbon. The apparatus can include air flow devices such as ventilators configured to change the air in the chamber in a time period less than two minutes, typically less than or equal to one minute. In some embodiments, the chamber volume approximates 100 liters and a ventilator is included, such as a ventilator that generates a gas flow of at least 1600 liters/min. One or more environmental controls can be included such as to control pressure, temperature and/or humidity in the area surrounding the tubular member during fiber matrix application. In some embodiments, temperature is maintained between 18° C. and 22° C. In some embodiments, relative humidity is maintained between 25% and 50%.

The apparatus can include a misting assembly, such as a misting assembly configured to apply a mist prior to application of the fiber matrix, during application of the fiber matrix, or after application of the fiber matrix. The applied mist can include at least one functional components selected from the group consisting of: a hydrating agent; a nutrient; an antimicrobial agent; and a vasorelaxing agent such as papaverine. The mist can be constructed and arranged to achieve at least one of: maintenance of the tubular member in a properly hydrated state; inclusion of metabolites in the graft device; contamination reduction; sterility improvement; relaxation of smooth muscle cells such as to reduce trauma to the tubular member; or buffering of the tubular member against changes in pH induced by a polymer, solvent, or other polymer solution component.

The apparatus can include a marking assembly, such as an assembly constructed and arranged to create a mark on the fiber matrix or the tubular member. The marking assembly can comprise a laser, and can provide information relative to venous valve flow direction when the tubular member comprises a vein segment. The apparatus can include an agent delivery assembly, such as a delivery assembly constructed and arranged to deliver a drug selected from the group consisting of: time release drugs; anti-clotting drugs such as heparin, aspirin and clopidogrel; vasoactive drugs and molecules such as nitric oxide, carbon monoxide, papaverine, norepinephrine and sodium nitroprusside; antibiotics; anti-proliferative agents; analgesics such as acetaminophen, naproxen, ibuprofen; and combinations thereof. Alternatively or additionally, the agent delivery assembly can be constructed and arranged to deliver a cell selected from the group consisting of: endothelial cells; mesenchymal stem cells; endothelial progenitor cells; hematopoietic stem cells; bone marrow-derived progenitor cells; other adult stem cells; embryonic stem cells; and combinations thereof. In some embodiments, the delivered agent is a vasoconstrictor such as norepinephrine, CO or NO. In some embodiments, the delivered agent is an adhesive such as fibrin glue. Alternatively or additionally, in some embodiments, the agent is constructed and arranged to adjust or trigger biodegradation of the fiber matrix. The agent delivery assembly can deliver agents encapsulated in microspheres, and it can deliver an agent configured to protect the tubular member and/or the fiber matrix from a solvent.

The apparatus can include an emergency shutoff, such as a manual or automatic shutoff triggered to discontinue one or more apparatus function with the detection of: process parameter out of an expected value range; loss of power; temperature or humidity out of an accepted value range; presence of fiber at an unacceptable location; lack of sufficient flow of polymer solution to nozzle; nozzle or mandrel voltage at an unacceptable level; displacement of internal components; and combinations of these.

According to another aspect, a method of applying a restrictive fiber matrix to a tubular member to create a graft device is provided. A rotating assembly is provided for rotating the tubular member. A polymer delivery assembly is provided to deliver fiber, such as electrospun polymer fiber, to the tubular member. A controller is provided to control the polymer delivery assembly and the rotating assembly. The method can include harvesting a vessel, from the patient receiving the graft device or another mammalian source. An imaging or other diagnostic procedure can be performed, such as to gather patient anatomical or other patient information. In some embodiments, the harvested vessel comprises a saphenous vein segment selected based on a patient image such as an angiographic or MRI image. In some embodiments, the fiber matrix is applied in an electrospinning process and the gathered patient information is used to modify one or more electrospinning process parameters. In some embodiments, a mandrel is selected, such as a mandrel selected from a group of mandrels based on patient anatomy or other patient information.

The method can include mixing and/or filtering polymer solution for delivery to one or more selected nozzles, such as nozzles configured for electrospinning the fiber matrix around the tubular member. One or more agents can be applied to the mandrel, tubular member and/or fiber matrix, such as a vasoconstricting agent such as norepinephrine, CO and/or NO applied to create a uniform diameter of the tubular member such as by reducing pleating of a harvested vein wall.

The method can include lowering the temperature of the tubular member, such as when the tubular member comprises living tissue such as a vein harvested from the patient receiving the graft device. The temperature can be lowered prior to, during and/or after application of the fiber matrix, such as to a temperature approximating 4° C.

The method can include entering input data into the apparatus, such as data input manually and/or automatically and typically selected from the group consisting of: mandrel OD; tubular member data such as tubular member length; patient data such as patient physiologic data; environmental data such as temperature and/or humidity data; and combinations of these. One or more fiber matrix delivery parameters can be maintained, modified or otherwise controlled by the controller during application of the fiber matrix. Typical fiber delivery parameters controlled include but are not limited to: electric potential at a nozzle; electric potential at the tubular member and/or mandrel; mandrel rotation speed and direction; nozzle translation speed; distance of nozzle to mandrel; polymer solution composition including polymer types, solvent types and relative concentrations; and combinations of these. One or more fiber delivery parameters can be modified during application of the fiber matrix such as to modify the fiber matrix along the length and/or through the thickness (e.g. a different inner layer than outer layer). The one or more parameters can be changed automatically and/or manually such as at a particular time selected from the group consisting of: a temporal value such as time elapsed since fiber delivery initiation; position of nozzle relative to tubular member such as position relative to a sidebranch or an end of the tubular member; current thickness of fiber matrix in the application process such as a factor that changes near the beginning of the fiber application or near the completion of the fiber application; environmental condition such as temperature or humidity value; and combinations of these. In some embodiments, the fiber delivery process is modified at a side branch location of a harvested vessel tubular member, such as to reduce internal lumen variations proximate the side branch location.

The method can include controlling the environment surrounding the tubular member, such as controlling the environment surrounding the tubular member prior to, during and/or after the application of the fiber matrix. The method can include placing the tubular member on a mandrel and inserting the mandrel into a cartridge device. The apparatus can control the environment within the cartridge, such as by maintaining at least one of: pressure; temperature or humidity. The apparatus can continually exchange the gas in the cartridge or other chamber, such as within two minutes, typically within one minute.

The method can include translating a nozzle along the tubular member, and/or translating the tubular member in reference to the tip of a nozzle. The translation can occur at a rate between 100 mm/sec and 300 mm/sec, typically at a rate of approximately 200 mm/sec. The translation can include locations that allow fiber to be deposited beyond the length of the tubular member, such as to deliver fibers at least 1 cm beyond the end of the tubular member. The apparatus can rotate the mandrel during the fiber application, such as to cause a full circumferential fiber matrix to be created. Alternatively or additionally, one or more nozzles can rotate around the nozzle. Each nozzle can deliver one or more fibers simultaneously, such as approximately five fibers simultaneously.

The method can include applying an agent to the mandrel, the tubular member and/or the fiber matrix. The agent can be applied prior to application of the fiber matrix, during application of the fiber matrix and/or after application of the fiber matrix. The agent can comprise an imaging agent, such as a radiopaque substance, a fluorescent substance, and/or a magnetic or paramagnetic material. The agent can comprise a drug such as a drug selected from the group consisting of: time release drugs; anti-clotting drugs such as heparin, aspirin and clopidogrel; vasoactive drugs and molecules such as nitric oxide, carbon monoxide, papaverine, norepinephrine and sodium nitroprusside; antibiotics; anti-proliferative agents; analgesics such as acetaminophen, naproxen, ibuprofen; and combinations of these. The agent can comprise a cell, such as a cell selected from the group consisting of: endothelial cells; mesenchymal stem cells; endothelial progenitor cells; hematopoietic stem cells; bone marrow-derived progenitor cells; other adult stem cells; embryonic stem cells; and combinations of these. The agent can comprise a vasoconstrictor, an adhesive such as fibrin glue, an agent configured to adjust biodegradation, an agent encapsulated in microspheres and/or an agent configured to protect one or more graft device portions from a solvent.

The method can include applying a mist, such as from a misting assembly that applies a mist to the mandrel, the tubular member and/or the fiber matrix. The mist can be applied prior to the application of the fiber matrix, during application of the fiber matrix and/or after application of the fiber matrix. The mist can comprise at least one agent selected from the group consisting of: a hydrating agent; a nutrient; an antimicrobial agent; and a vasorelaxing agent such as papaverine. The mist agent can be configured to achieve at least one of: maintenance of the tubular member in a properly hydrated state; inclusion of metabolites in the graft device; contamination reduction; sterility improvement; relaxation of smooth muscle cells such as to reduce trauma to the tubular member; or buffering of the tubular member against changes in pH induced by a polymer, solvent, or other polymer solution component.

The method can include changing one or more properties of the tubular member, the fiber matrix or another portion of the graft device. The change can occur prior to application of the fiber matrix, during application of the fiber matrix and/or after the fiber matrix is applied. The change can be implemented through the delivery of energy, such as energy selected from the group consisting of: cryogenic or other cooling energy; heat; UV radiation; radiofrequency energy; microwave energy; ultrasound energy; laser energy; and combinations of these. The method can include the performance of a diagnostic procedure, such as a diagnostic procedure performed on a mandrel, the tubular member, the fiber matrix and/or a portion of the graft device. Alternatively or additionally, the diagnostic procedure can be a patient diagnostic procedure. The diagnostic procedure can be a measurement procedure, such as a procedure performed with a laser micrometer or camera system. The method can further include adjusting a fiber matrix delivery parameter based on data produced during the diagnostic procedure. The method can further include delivering an agent or applying energy as a result of the data produced during the diagnostic procedure.

The method can include removing the graft device from a mandrel, such as a removal involving cutting through at least a portion of the fiber matrix.

The method can include a preferred order of initiating an electrospinning process to deliver fiber to the tubular member. At least one of activating an electric field between a nozzle and the tubular member; starting rotation of the tubular member; or starting translation of a nozzle can be performed prior to starting flow of a polymer solution to the nozzle.

The method can include a preferred order of stopping an electrospinning process to deliver fiber to the tubular member. At least one of: deactivating an electric field between a nozzle and the tubular member; stopping rotation of the tubular member; or stopping translation of a nozzle, can be performed after stopping flow of a polymer solution to the nozzle.

BRIEF DESCRIPTION OF THE DRAWINGS

The accompanying drawings, which are incorporated in and constitute a part of this specification, illustrate various embodiments of the systems and methods described herein, and together with the description, serve to explain the principles of the systems and methods described herein. In the drawings.

DETAILED DESCRIPTION OF THE DRAWINGS

Figure 1:
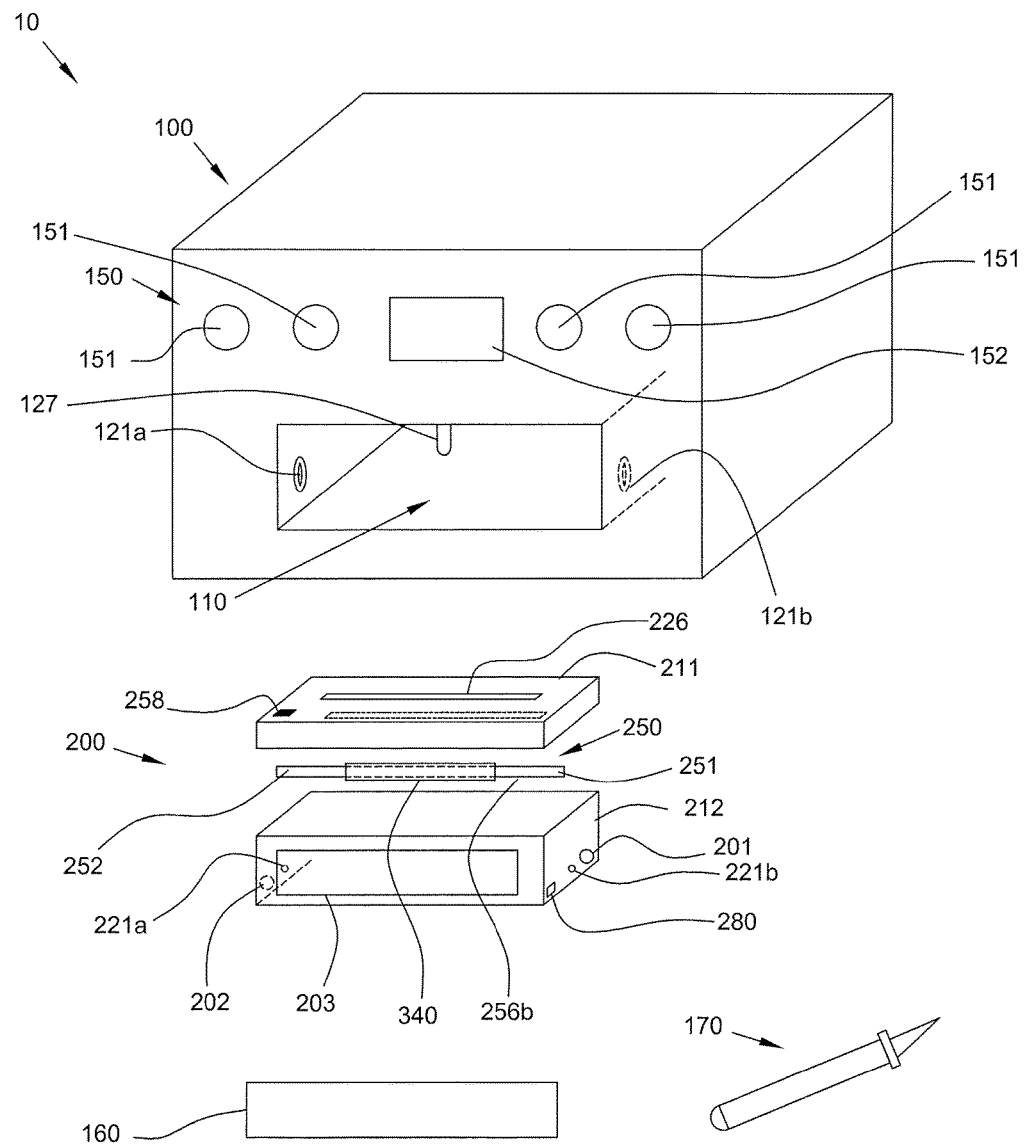
FIG. 1 illustrates a perspective view of an example apparatus for applying a fiber matrix to a tubular member.

Reference will now be made in detail to specific example embodiments, examples of which are illustrated in the accompanying drawings. Wherever possible, the same reference numbers will be used throughout the drawings to refer to the same or like parts.

Provided herein is an apparatus for applying a restrictive fiber matrix to a tubular member. A cartridge device can be included for insertion into a fiber application unit, such as an electrospinning unit or other piece of equipment constructed and arranged to apply a fiber, such as a polymer fiber, around at least a portion of the outer surface of a tubular member, such as a harvested blood vessel. The cartridge device comprises a housing that defines a chamber. Alternatively, the fiber application unit can include a housing that defines a chamber. A tubular member holder, such as a mandrel, slidingly receives the tubular member and the assembly is then inserted into the chamber. The fiber application unit includes a rotational drive mechanism such as a drive including one or more motors, which rotate the assembly of the mandrel and tubular member. While rotating, one or more types of fibers, such as polymer fibers, are delivered by a polymer delivery assembly, typically through at least one nozzle that translates back and forth in an oscillating motion along the length of the tubular member as fiber is applied. One or more nozzles can be included, and each nozzle can deliver a single fiber, or multiple fibers, simultaneously. The cartridge or other chamber is sterile and maintains sterility of the tubular member and applied fiber throughout the process.

The graft device produced by the devices, methods and apparatuses described herein includes a tubular member and a surrounding fiber matrix covering. The tubular member is typically a hollow tube conduit used as a connection for fluid to flow between a first body space and a second body space. The tubular member can comprise tissue, such as autologous, allogeneic, or xenogeneic tissue, including, without limitation: vein; artery; lymphatic duct; vas deferens; tear duct; intestine; esophagus; ureter; urethra; trachea; bronchi; duct tissue; Eustachian tube; fallopian tube; and combinations of these (meaning the entire structure or a portion of those tissues). The tubular member can also be a tissue engineered vascular graft, comprised of a covering material (biological or synthetic-based) that is seeded with adult differentiated cells and/or undifferentiated stem cells, or unseeded. The covering can be treated with synthetic, biological, or biomimetic cues to enhance anti-thrombogenicity or selective or non-selective cell repopulation once implanted in vivo. The covering can be treated with one or more chemotactic or chemoattractant agents and can include selective degradation sites. Alternatively or additionally, the tubular member can include an artificial, non-tissue, structure, such as polytetrafluoroethylene (PTFE); expanded PTFE (ePTFE); polyester; polyvinylidene fluoride/hexafluoropropylene (PVDF-HFP); silicone; polyethylene; polypropylene; polyester based polymer; polyether based polymer; thermoplastic rubber; and combinations of these. The graft device can have a relatively uniform cross section, or a cross section that varies (e.g. in diameter or cross sectional geometry) along the length of the tubular member. The graft device can be straight or curved. Additional graft devices, apparatus and methods are also described in applicant's co-pending PCT Patent Application Serial No. PCT/US2010/60667, filed Dec. 16, 2010, entitled "Graft Devices and Methods for Use," applicant's co-pending U.S. Provisional Patent Application Ser. No. 61/291,820, filed Dec. 31, 2009, entitled "Graft Devices and Methods of Fabrication", and applicant's co-pending U.S. Provisional Patent Application Ser. No. 61/365,612, filed Jul. 19, 2010, entitled "Graft Devices and Methods of Use", the contents each of which are incorporated by reference herein in its entirety.

The applied fiber is typically a polymer or polymer blend fiber that is applied when the one or more polymers are mixed with one or more solvents. Alternatively or additionally, polymers can be applied in liquid form achieved through other means such as by elevated temperature or by the use of monomers which are activated and polymerized during or shortly after processing. Typical polymers include natural polymers, synthetic polymers, and blends of natural and synthetic polymers. For example and without limitation, natural polymers include silk, chitosan, collagen, elastin, alginate, cellulose, polyalkanoates, hyaluronic acid, and gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers.

As used herein, the descriptor "tubular member" does not refer specifically to a geometrically perfect tube having a constant diameter and a circular cross-section. It also embraces tissue and artificial conduits having non-circular and varying cross sections, and can have a variable diameter, and thus any shape having a contiguous wall surrounding a lumen (that is, they are hollow), and two openings into the lumen such that a liquid, solid or gas can travel from one opening to the other. The tubular member can be created from a membranous material, such as a membrane that comprises a sheet that is joined along a seam to create a substantially cylindrical form. The tubular member can comprise harvested tissue that is formed or reformed into a tube or other structure.

The covering typically is substantially or essentially contiguous about an internal or external wall of a tubular member, meaning that the covering forms a continuous, supportive ring on a surface and about a circumference of a portion, but not necessarily over the entire surface (e.g., length) of the tubular member. The covering can be "restrictive", meaning that the covering is in substantial contact with the outer surface of the tubular member such as to provide an incremental physical property in addition to the underlying property of the tubular member. Alternatively, the covering can be narrowly spaced and proximate to the outer surface of the tubular member (e.g. to restrict after an initial unrestricted expansion). The covering can also be "constrictive", meaning that the diameter of the tubular member is reduced by the application of the covering. Restrictive coverings can be used to reinforce, restrict, hinder and/or prevent substantial circumferential and/or longitudinal expansions of the tubular member, such as when the graft device is a tubular member used as a bypass graft and is exposed to arterial pressure; or otherwise when the tubular member is radially and/or longitudinally expanded. The degree of restriction by the covering typically is such that when exposed to internal pressure, such as typical arterial pressures, the tubular member is prevented from distending to the extent that would occur without such restriction. Constrictive coverings can be used to match the internal diameter of the tubular member to the internal diameter of the target tissue being connected by the tubular member. For example, quite often a vein being used as a coronary artery bypass graft has a considerably larger internal diameter than the target coronary artery being bypassed. In order to reduce flow disturbances, it is advantageous to match the internal diameter of the graft (conduit) to the internal diameter of the bypassed coronary artery. The covering can be durable or temporary, such as when the restrictive nature of a biodegradable covering can decline over time. The covering can have a relatively uniform cross section, or a cross section that varies along the length of the covering.

The covering can be applied to a tubular member that has either a cylindrical or non-cylindrical (e.g. oval) mandrel inserted in its lumen. Mandrels are typically constructed and arranged to be removed from the graft device without damaging the tubular member or any other portion of the graft device. The mandrel can comprise an expandable tube, such as a furled tube or other radially or axially expandable structure, such that the mandrel can be unfurled or otherwise radially or axially constricted for atraumatic removal from the tubular member of the graft device. The mandrel can transform from a rigid state to a flexible state, and vice versa. Mandrels can have relatively constant cross-sectional geometries, or cross-sections that vary, such as mandrels including a first portion with a circular cross sections and a second portion with an oval cross sections; and tapered mandrels.

The mandrel can be relatively straight, or can have a non-linear geometry. In some embodiments, a mandrel comprises a three dimensional geometry intended to match anatomical locations of a patient, such as an anatomical topography proximate two or more intended anastomotic connections for the graft device. Mandrels can include both straight and curved portions. The mandrel can be a malleable or otherwise deformable structure which is shaped during a surgical procedure. Alternatively, the mandrel can be fabricated based upon one or more patient images created during an imaging procedure, such as an imaging procedure selected from the group consisting of: X-ray such as still image X-ray or fluoroscopy; MRI, CT scan, NMR, ultrasound, PCT scan, CCD camera; film camera; and combinations of these.

In coverings applied to a tubular member with an electrospinning process, an electrically conductive mandrel, for example a rod that is formed of a conductive material such as stainless steel, can be placed inside a tubular member, such as a vein, and polymer fibers deposited about the circumference of at least a portion of the tissue by rotation or other movement of the mandrel, movement of the nozzles supplying the fiber, and/or movement of the electrical field directing the fibers toward the mandrel. Thickness, as well as other mechanical and physical properties of the covering, can be controlled by adjusting the chemical or physical properties of the polymer solution to be deposited (e.g. adjusting the conductivity, surface tension and/or viscosity of the solution), increasing the infusion rate of the polymer solution, modifying the electric field between the polymer source and the mandrel or target, and/or adjusting duration of the electrospinning Use of more or less viscous polymer compositions can result in thicker or thinner fibers, respectively, affecting the mechanical properties (e.g. the elastic, viscoelastic, and plastic properties), the level of polymer crystallinity, the solvent content (the amount and feature of nodal points obtained by solvent bonding also affects the mechanical and physical properties of the material), and the porosity of the deposited polymer. The thickness of the covering and fibers within the covering can be selected to determine numerous device properties including but not limited to: stiffness and buckling stability; mechanical stability under sustained levels of stress of cyclic deformations; speed of biodegradation of the covering; permeability of the material; and combinations of these. Biodegradation can also be varied by altering the surface finish, wettability, porosity or other characteristic of the fibers, as well as by introducing functional domains to the fiber matrix structure (e.g., cleavage domains activated in response to natural or artificial cues). These parameters can be altered by using solvents or diluents that evaporate at varying rates and/or by adding purifiers to the solution, such as immiscible fluids, emulsified particles or undissolved solids that can be later dissolved such as to create pores. Alternatively or additionally, other modifying agents can be added to the polymer prior to electrospinning such as detergents or surfactants. These polymer solution parameters are optimized, depending on the end-use of the covering, to achieve a desired or optimal physiological effect. Functional domains can be added by covalent bonding to the fiber matrix structure. Thickness and other features (e.g. fiber size, porosity, nodal points, fiber crystallinity or mechanical properties) can be varied along the length of a target in a regular or irregular fashion, such as in creating a target that is thicker at one or both ends, in the center or as with a location-dependent symmetrical or asymmetrical thickness. In some embodiments, the thickness is varied by moving an electrospinning nozzle back in forth slowly near a specific circumferential location, thereby depositing more material proximate to that area or to create recurring features. In some embodiments, covering thickness is determined by the thickness of the tubular member, such as when the covering is thicker at a circumferential portion of the tubular member that is thinner than other circumferential portions of the tubular member. In some embodiments, thickness and/or other properties are varied by applying a field modification proximate to the polymer source or target to alter the trajectory of the fibers. Such a field modification could be produced for example by a metal plate that is inserted into the area adjacent to the source or target that is at a sufficiently different voltage potential than the source such that the resulting field alters the trajectory of the fibers.

Electrospinning can be performed using two or more nozzles, wherein each nozzle can be a source of a different polymer solution. The nozzles can be biased with different biases or the same bias in order to tailor the physical and chemical properties of the resulting non-woven polymeric mesh. Additionally, multiple different targets (e.g. mandrels) can be used. When the electrospinning is to be performed using a polymer suspension, the concentration of the polymeric component in the suspension can also be varied to modify the physical properties of the matrix. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower polymer concentration solutions have a lower viscosity, leading to greater extrusion or attenuation of the fibers to produce thinner fibers. One skilled in the art can adjust polymer solution chemical and physical properties and process parameters to obtain fibers of desired characteristics, including fibers whose characteristics change along the length or width of the target.

Coverings can be constructed and arranged in a manner specific to a patient morphological or functional parameter. These parameters can be selected from the group consisting of: vessel size such as inside diameter, outside diameter, length, and/or wall thickness; taper or other geometric property of a harvested vessel or vessel intended for anastomotic attachment; size and location of one or more side branch ostium or antrum within the harvested vessel; patient age or sex; vessel elasticity or compliance; vessel vasculitis; vessel electrical impedance; specific patient genetic factors or traits, specific patient pathologies; and combinations of these.

Coverings of arterial vein grafts can be processed in a way to achieve a certain blood flow rate or shear stress within the treated arterial vein graft. In a typical configuration, shear stress within the arterial vein graft is between 2 dynes/cm$^2$ to 30 dynes/cm$^2$ (e.g., 12 dynes/cm$^2$ to 20 dynes/cm$^2$) is achieved. Coverings can be processed in a way to control the oxygen, nutrients, or cellular permeabilities between the extravascular tissues and the abluminal surface of the treated hollow tissue. Such permeabilities depend on the covering chemical and physical properties, the pore size distribution, porosity, and pore interconnectivity. Generally, oxygen, nutrients, and cellular (e.g., angiogenesis related cells, pericytes, endothelial cells, endothelial progenitor cells, inflammation-related cells; macrophages, etc.) permeability are required to improve the treated hollow tissue in vivo remodeling and healing process. To this end the pore size range is typically between 1 microns and 1000 microns, preferably between 100 microns and 250 microns, and the porosity range typically between 50% and 95%, preferably between 60% and 90%. The pores preferably are highly interconnected so that a relatively straight path along the radial direction of the fiber matrix can be traced from most of the pores across the total thickness of the matrix. Polymers used are typically hydrophobic.

Radial restriction and constriction of saphenous vein grafts has been achieved with stent devices placed over the vein prior to anastomosing the graft to the targeted vessels. The devices described herein can provide numerous advantages over the stent approaches. The devices described herein can have one or more parameters easily customized to a parameter of the harvested vessel and/or another patient parameter. The covering can be customized to a harvested vessel parameter such as geometry, such as to reduce the vein internal diameter to produce desired flow characteristics. The covering can be customized to other harvested vessel parameters such as the number and location of side branches or other vessel irregularities, such as to produce an internal lumen with a consistent size along the length of the graft despite the external irregularities of the harvested vessel. The covering can be customized to a target vessel parameter (e.g., the aorta and diseased artery), such as to be compatible with vessel sizes, mechanical properties, and/or locations. The covering can be modified to simplify or otherwise improve the anastomotic connections, such as to be reinforced in the portion of the device that is anastomosed (e.g., portion where suture and/or clips pass through) and/or to protrude beyond the length of the tubular member and overlap other members connected to the graft device.

The devices described herein can be made to a wide array of lengths during the procedure, without the need for cutting, such as the cutting of a stent device, which might create dangerously sharp edges. The covering is applied to the tubular member in a controlled, repeatable manner, by an apparatus such as an electrospinning instrument. The ends of the covering are atraumatic, avoiding tissue damage or irritation at the anastomotic sites. In addition, the coverings can be constructed and arranged to be easily and atraumatically removable, such as to apply another covering. Stent devices are typically applied manually by a clinician, require significant manipulation which could cause iatrogenic damage, have issues with reproducibility and accuracy limitations, and are difficult to reposition or remove, particularly without damaging the harvested vessel. The conformal covering follows the natural external geometry of the vessel (e.g., adventitial tissue accumulations, ligated branches, etc.) without resulting in a net inward compression caused by external application of a constant tubular structure onto a naturally variable tubular tissue.

As used herein, the term "polymer composition" is a composition comprising one or more polymers. As a class, "polymers" includes homopolymers, heteropolymers, co-polymers, block polymers, block co-polymers, alloys or blends and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, fibrin, chitosan, collagen, elastin, alginate, cellulose, polyalkanoates, hyaluronic acid, and gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers, block polymers, and block co-polymers.

The polymer or polymers typically will be selected so that it degrades (e.g. it is bioabsorbed, has decreased mechanical strength and/or otherwise changes one or more mechanical properties) in situ over a time period to optimize mechanical conditioning of the tissue or other tubular member. Non-limiting examples of useful in situ degradation rates include between 2 weeks and 1 year, and increments of 1, 2, 4, 8, 12, and 24 weeks therebetween. Biodegradation can occur at different rates along different circumferential and/or axial portions of the covering. A biodegradation rate of the polymer covering can be manipulated, optimized or otherwise adjusted so that the covering degrades over a useful time period. For instance, in the case of a coronary artery bypass, it is desirable that the covering dissolves over 2 weeks or, more typically, 10 weeks or more, so as to prevent substantial sudden circumferential wall stress on the graft. The polymer degrades over a desired period of time so that the mechanical support offered by the polymer covering is gradually reduced over that period and the vein would be exposed to gradually increasing levels of circumferential wall stress (CWS).

The biodegradable polymers useful herein also can be elastomeric. Generally, any elastomeric polymer that has properties similar to that of the soft tissue to be replaced or repaired is appropriate. For example, in some embodiments, the polymers used to make the wrap are highly distensible. Non-limiting examples of suitable polymers include those that have plastic yield strain of 10% to 100% and breaking strain of from 100% to 1700%, more preferably plastic yield strain between 15% and 100%, and breaking strain between 200% and 800%, and even more preferably plastic yield strain between 50% and 100%, and breaking strain between 200% and 400%. Further, it is often useful to select polymers with ultimate tensile stress between 10 kPa and 30 MPa, more preferably between 5 MPa and 25 MPa, and even more preferably between 8 MPa and 20 MPa. In some embodiments, polymeric fiber matrices with plastic yield tensions between 1 N/cm and 10 N/cm, preferably between 2 N/cm and 5 N/cm are used. In some embodiments, the elastic modulus calculated for physiologic levels of strain is between 10 kPa to 100 MPa, (e.g., between 0.5 MPa and 1.5 MPa (e.g., between 0.5 MPa and 1.0 MPa)).

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, a "fiber" comprises an elongated, slender, thread-like and/or filamentous structure with or without branching fibers. Fibers can be solid (including composite materials such as concentric or particulate-included composite materials) or hollow, and can have a smooth, rough, or porous surface.

As used herein, a "matrix" is any two- or three-dimensional arrangement of elements (e.g., fibers), either ordered (e.g., in a woven or non-woven mesh) or randomly-arranged (as is typical with a mat of fibers typically produced by electrospinning).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

Referring now to FIG. 1, a perspective view of an apparatus is illustrated. Apparatus 10 comprises electrospinning unit 100 and cartridge 200 and is constructed and arranged to produce a graft device. A tubular member, conduit 340, is placed over mandrel 250, typically centered along the length of mandrel 250, and placed within cartridge 200. Conduit 340 can comprise living tissue, such as tissue of the patient selected to receive the graft device, and/or it can comprise an artificial material, examples of each described in detail hereinabove.

Electrospinning unit 100 comprises slot 110 that is sized and positioned to accept cartridge 200. Electrospinning unit 100 further comprises drive elements 121a and 121b that include one or more rotational drive components configured to rotate in synchrony. Drive elements 121a and 121b can be synchronized with the use of a timing pulley. Alternatively, or additionally drive elements 121a and 121b can comprise two motors synchronized and/or otherwise controlled with optical encoders. Alternatively, a single drive element 121a can be incorporated, configured to drive a conduit holder of cartridge 200 from one end, such as at drive end 252 of mandrel 250. Drive elements 121a and 121b can include numerous drive assembly components including but not limited to: a bearing such as a magnetically levitated bearing, a ball bearing, an air bearing or a pin bearing; a bushing; a torsion spring such as a torsion spring which is oscillated at its resonant frequency; a motor such as a DC motor, AC motor, synchronous motor or stepper motor, a gear box; and combinations of these. In some embodiments, mandrel 250 is rotated at approximately 250 rotations per minute as the fiber matrix is applied to the tubular member.

Cartridge 200 comprises mandrel 250 and a surrounding housing 210, reference number not shown on FIG. 1 but defining a chamber and comprising upper housing 211 and lower housing 212. Mandrel 250 is sized and configured to slidingly receive a tubular member such as a saphenous vein graft. Cartridge 200 is slidingly received by slot 110 of electrospinning unit 100. Mandrel 250 can or can not be geometrically centered in the surrounding housing 210.

Cartridge 200 further comprises an internal chamber and an exterior surface between which a sterility barrier can exist. Alternatively, the entire cartridge 200 can be maintained sterile through its use. Housing 210, or a portion such as the exterior surface of housing 210, can comprise an equipotential conductive surface such as a surrounding conductive surface defining a Faraday cage. The equipotential surface can be achieved with various elements including conductive paints or coatings, or a conductive substance included in the housing material. The exterior surface can carry a positive, negative, or zero-potential (ground) charge. Housing 210 can include an insulating layer on its interior surface, such as an insulating surface comprising activated carbon.

Cartridge 200 comprises bar code 258 that is readable by electrospinning unit 100 (barcode reader not shown) and provides an identifier, such as a unique identifier, for cartridge 200. Information included in bar code 258 can be used by electrospinning unit 100 to adjust one or more electrospinning or other graft device creation process parameters; log use; prevent second or other repeated use; log other information; and the like. Bar code 258 can include information relative to the diameter or other geometric parameter of mandrel 250.

Mandrel 250 is comprised of end 251 and drive end 252 that pass into receiving holes 221a and 221b of housing 210. Drive element 121a and drive element 121b of electrospinning unit 100 engage end 252 and end 251, respectively, such as to rotate mandrel 250 during the application of the fiber during the electrospinning process. End 252 and/or 251 can have a non-circular surface such as to securely engage on their outer surface drive elements 121a and 121b, respectively. Alternatively or additionally, end 251 and/or 252 can include a recess, such as a square, rectangular, hexagonal or elliptical recess to securely engage one or more mating projections of drive elements 121a and/or 121b.

A voltage is applied to mandrel 250, such as a voltage applied to drive end 252 via drive element 121a of electrospinning unit 100. Voltage applied to mandrel 250 can be constant or varying, and is configured to create an electric field sufficient to direct a stream of fiber toward mandrel 250, such as from a polymer delivery assembly including nozzle 127 of electrospinning unit 100. A voltage is applied to nozzle 127 that is at a different potential than the voltage applied to mandrel 250, typically creating a voltage potential difference greater than 1000 Volts. Applied voltage can be uniform across the length and circumference of mandrel 250, or it can vary. Applied voltage can be different at a mid portion of mandrel 250 as compared to one or more end portions, such as when a mid portion is at a higher voltage than one or more end portions. In a preferred embodiment, nozzle 127 voltage is charged to +15 kV, while conduit 340 or mandrel 250 is charged to −5 kV. Mandrel 250 can be constructed of a conductive material, a resistive or other semi-conductor material, or both. Mandrel 250 can have a different conductivity at one or more portions, such as a mandrel with a different conductivity at a mid portion when compared to an end portion. One or more masks can be included on the surface of mandrel 250, such as an insulating or semi-conductive mask applied to one or both end portions of mandrel 250. The mask can be permanently affixed, or it can be attachable and/or removable. Mandrel 250 is typically 30-35 cm in length, with an outer diameter configured to support various sizes of tubular members. In some embodiments, mandrels are typically supplied with a range of diameters between 2 mm and 6 mm, typically between 2 mm and 4 mm. Multiple mandrels with different lengths or other differences can be included in apparatus 10. In some embodiments, electrospinning unit 100 or another component of apparatus 10 automatically detects the size of mandrel 250, such as through the use of bar code 258, a separate barcode on mandrel 250, or by other detection means. The size of mandrel 250 can be used, whether detected automatically or entered manually by a user, to adjust one or more electrospinning or other process parameters, such as a parameter selected from the group consisting of: nozzle translation speed; nozzle distance from mandrel 250; polymer flow rate; process time; and combinations of these. Mandrel 250 can be stainless steel, can be a passivated metal, and can comprise a surface finish of smoother than or equal to 5 μm.

Housing 210 comprises upper housing 211 and lower housing 212. Upper housing 211 and/or lower housing 212 can be transparent or include one or more transparent portions. These transparent portions allow visible or other light to pass through, such as to allow operation of an optical measurement assembly 160, such as a laser micrometer or a camera such as a high resolution camera. Visualization devices can be used for many purposes including but not limited to visualizing the position of a cartridge component and visualization of the polymer stream when directed toward the conduit holder, mandrel 250. Visualization information can be processed to provide feedback and adjust one or more apparatus parameters in real time. Measurement device 160 can be positioned to view the fiber matrix deposition process including the path of the fiber toward mandrel 250, such as via transparent window 203 of lower housing 212. In some embodiments, the entire construction of lower housing 212 and/or upper housing 211 is transparent.

Ports 201 and 202 are typically included in the side walls of housing 210 and can provide a connection to an external environmental control device. Ports 201 and 202 can include a covering, such as a removable Tyvek patch, or can include a resealable membrane. Electrospinning unit 100 can include an environmental control assembly, such as an assembly that maintains temperature, humidity, barometric pressure, and/or certain gas mixtures partial pressures, and be attachable to one or more of ports 201 and 202 of cartridge 200. Typical environmental control devices include but are not limited to: a positive pressure source; vacuum source; gas mixture source, heating unit; cooling unit; humidifier; dehumidifier; ventilation fan; gas composition probe, HEPA filtration, halogenated gas absorbent filter, and combinations of these. One or more inert gases such as sterilized air or nitrogen can be passed through ports 201 and/or ports 202. In some embodiments, the electrospinning process is performed with temperature maintained between 18° C. and 22° C., and relative humidity maintained between 25% and 50%. Additionally, apparatus 10 can include a ventilation fan to ventilate gases contained within cartridge 200, such as a ventilation fan producing a nominal flow rate of approximately 1,600 liters per minute and typically scaled down to approximately 100-200 liters per minutes by filtration units. In some embodiments, the gas in a chamber (e.g. housing 210) surrounding mandrel 250 is continuously replaced or exchanged, such as during a period of less than two minutes, typically less than one minute. In some embodiments, a chamber surrounding mandrel 250 is approximate 80 liters to 140 liters in volume, such as approximately 100 liters in volume. In some embodiments, a chamber surrounding mandrel 250 has dimensions approximating 40 cm deep, 50 cm long and 40 cm high.

Housing 210 also includes sensor 280. Sensor 280 can be located in one or more positions of cartridge 200 or electrospinning unit 100, is operably connected to electrospinning unit 100, and can comprise multiple sensors such as multiple sensors in multiple locations. Sensor 280 can be capable of measuring one or more process conditions including but not limited to: temperature; pressure; humidity; an aspect of the solvent or polymer such as an airborne solvent parameter; velocity (e.g. rotational and translational); diameter; electric field direction or magnitude; a force such as a force applied to the conduit holder to create tension; impedance of the tubular tissue; electrical current generated by the transportation of charge by the carrier polymer solution; thickness of the applied fiber matrix; and combinations of these. Sensor 280 can be attachable, detachable, or integral to mandrel 250. In some embodiments, sensor 280 is a transducer, such as a light, heat, audio, pressure, magnetic, vibrational, and/or other transducer. Sensor 280 can be used to confirm integrity of one or more electrical connections, such as an electrical connection to a nozzle or conduit holder. Sensor 280 can be used to confirm integrity of one or more mechanical connections, such as a connection maintaining a fluid path between cartridge components.

Slot 226 is located on upper housing 211 such that at least one polymer fiber stream can be delivered from nozzle 127 to circumferentially cover the outside surface of conduit 340. The polymer fiber is delivered while an electric field is applied between nozzle 127 and mandrel 250, typically with mandrel 250 being rotated. Nozzle 127 can be integral to electrospinning unit 100 as shown and/or it can be integral to cartridge 200. In some embodiments, a polymer solution is provided to nozzle 127 at a flow rate of between approximate five mL/hour and seven mL/hour. In some embodiments, the polymer solution comprises polycaprolactone (PCL) which is mixed with a solvent, typically hexafluoroisopropanol (HFIP-1,1,1,3,3,3-Hexafluoro-2-propanol), at a concentration of 11.5% weight/volume (gm/mL). For example, 1.15 grams of PCL is dissolved into 10 mL of HFIP. Typically, the viscosity of the HFIP is 400 cST to 700 cST when measured at 20° C. to 22° C., and more typically 500 cST to 600 cST when measured at 20° C. to 22° C. The surface tension of the HFIP is typically between 21.5 dynes/cm and 22.5 dynes/cm when measured at 20° C. to 22° C. Prior to distribution to nozzle 127, the polymer solution or any component thereof can be filtered, such as with a 0.2 micron PTFE filter.

Electrospinning unit 100 includes a graphical user interface 150 comprising multiple user input components and user output components such as screen 152 and multiple controls 151. User interface 150 is constructed and arranged to operate the controller portions of electrospinning unit 100, as well as provide process and other information to one or more users of apparatus 10. Typical controller portions are configured to perform one or more of the following functions: control the polymer delivery; initiate and halt delivery of polymer solution to a nozzle; adjust polymer solution flow rate; mix polymer solution components; rotate one or more mandrels; translate one or more nozzles; rotate one or more nozzles; monitor the environment of an area surrounding the tubular member; maintain the environment of an area surrounding the tubular member such as to maintain pressure; temperature and/or humidity; apply an electrical potential between at least one nozzle and at least one mandrel; and combinations of these.

Controls 151 can include switches such as slide or membrane switches, or other controlling elements such as electrical, mechanical or electromechanical controlling elements. Screen 152 can be a touch screen display. Controls 151 and/or screen 152 are used to enter electrospinning settings or other input data. Screen 152, and one or more other output devices, not shown, but typically alphanumeric screens, lights such as LEDs, and transducers such as audible buzzers or speakers, provide information to the users of apparatus 10. User interface 150 can be used to enter data including but not limited to: mandrel size; nozzle speed; polymer solution flow rate; process time; and combinations of these. In one embodiment, a control 151 is an emergency shut off switch used to shut down the electrospinning process in an emergency situation. Alternatively or additionally, an emergency situation can be automatically detected by apparatus 10. Emergency conditions (e.g., emergency situations) include but are not limited to: process parameter out of an expected value range; loss of power; temperature or humidity out of an accepted value range; presence of fiber at an unacceptable location; lack of sufficient flow of polymer solution to nozzle; nozzle or mandrel voltage at an unacceptable level; displacement of internal components; and combinations of these.

While electrospinning unit 100 of FIG. 1 shows a single slot 110, multiple slots can be incorporated to process multiple cartridges 200 simultaneously or sequentially. The process of applying the restrictive fiber matrix to conduit 340 is typically completed within twenty minutes, more typically between ten and fifteen minutes. Once complete, cartridge 200 and/or mandrel 250 can be removed. Conduit 340 can be removed from mandrel 250 such as after cutting with a tool, such as scalpel 170. Scalpel 170 can be used to circumferentially cut the applied restrictive fiber matrix allowing conduit 340 to be slidingly removed from mandrel 250.

Figure 2A:
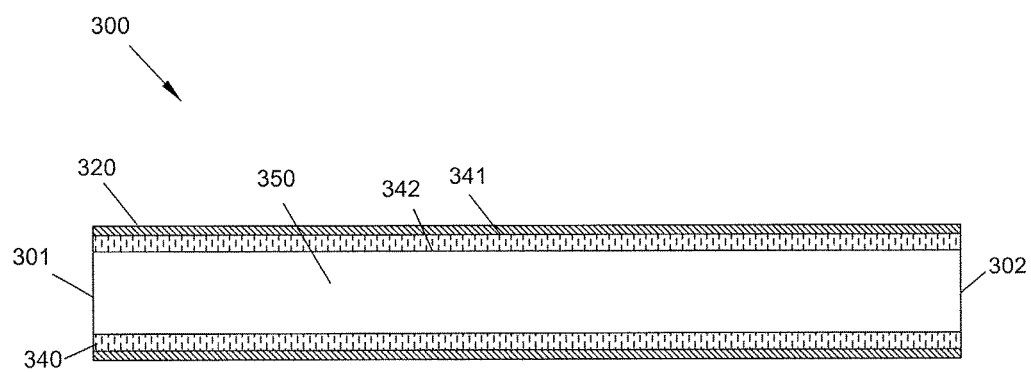
FIGS. 2A and 2B illustrate side and end sectional views of an example graft device comprising a fiber matrix covered tubular member.
Figure 2B:
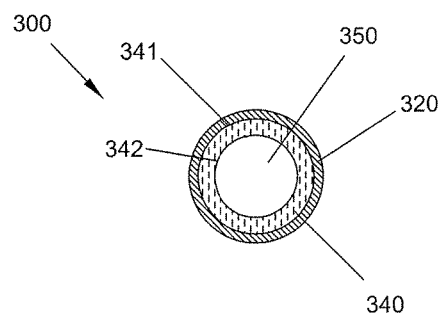

Referring now to FIGS. 2A and 2B, side sectional and end sectional views, respectively, of an example graft device. Graft device 300, biased in a relatively linear bias as shown, includes lumen 350 from first end 301 to second end 302. Graft device 300 also includes conduit 340 which is surrounded on its outer wall 341 by fiber matrix 320. Alternatively or additionally, covering 320 can surround the inner wall 342 of conduit 340. In some embodiments, a layer of material, not shown, but applied as described in reference to the apparatus of FIG. 4 herebelow, comprises an intermediate layer positioned between conduit 340 and fiber matrix 320. Alternatively or additionally, a material layer can be applied during another part of the graft device fabrication such as a material layer applied around a mandrel, for example mandrel 250 of FIG. 1, prior to its insertion into conduit 340; a material layer applied during application of fiber matrix 320; and/or a material layer applied on the outer surface of fiber matrix 320. Fiber matrix 320 can be a radially restrictive covering, such as a radially restrictive covering comprising a fiber matrix applied to conduit 340 during an electrospinning process, as has been described in detail in reference to FIG. 1 hereabove. A restrictive covering can be used to limit expansion (e.g. radial and/or longitudinal expansion) of conduit 340, such as when device 300 is used as a bypass graft in a cardiac bypass procedure. Similarly, the fiber matrix 320 can be constrictive (e.g. radially and/or longitudinally constrictive), such as a constrictive covering comprising a fiber matrix applied to conduit 340 during an electrospinning process. Fiber matrix 320 can be stretched (e.g. radially or longitudinally stretched) prior to application around conduit 340, such as with a tube expanding device. Fiber matrix 320 can be shrunk (e.g. radially and/or circumferentially shrunk) after placement around conduit 340, such as when fiber matrix 320 is a material constructed and arranged to radially shrink with the application of heat, light, chemicals or other agents, electric current, electromagnetic fields; and/or polymerization. Conduit 340 can include any tissue or artificial structure, such as has been described hereabove, or can include both tissue and artificial materials. One or more intermediate layers can be applied to provide a function, such as a function selected from the group consisting of: improved kink resistance; enhanced visibility such as to enhance visibility after implantation in a medical diagnostics imaging procedure; provide diagnostically imageable functional cues for conduit 340 mechanical properties; provide diagnostically imageable functional cues for one or more mechanical properties of conduit 340; provide functional cues for a fluid dynamic property of conduit 340; and combinations of these.

Graft device 300 is constructed and arranged to be placed between a first body space, such as a source of oxygenated arterial blood such as the aorta, and a second body space, such as a location distal to an occluded artery, such as an occluded coronary artery. In a typical embodiment, conduit 340 is a harvested vessel, such as a harvested saphenous vein graft. Graft device 300 can be processed after the application of fiber matrix 320. This processing can include cutting one or both of ends 301 and 302, such as to cut to a particular length. The cutting can be performed orthogonally or at an oblique angle (e.g. a spatulation cut), such as to improve creation and/or longevity of an anastomosis. The processing can include modifying one or both of conduit 340 and fiber matrix 320, such as to modify a surface or other parameter of conduit 340 or fiber matrix 320. Porosity can be modified, such as with a laser drilling device or mechanical puncturing device. Surface properties can be modified, such as with a laser or other etching process.

Fiber matrix 320 can have one or both of its end portions (portions proximate end 301 and end 302) modified or otherwise of different construction than the mid portion of fiber matrix 320. In some embodiments, at least one end portion of fiber matrix 320 is modified to support an anastomotic connection such as a connection achieved with suture, staples, or an anastomotic connector. The modification can include the end portions of fiber matrix 320 being thicker or thinner than the mid portion; the end portions being constructed of a different material or materials such as the inclusion of an increased tear resistant material such as the inclusion of a metal mesh; and combinations of these.

Conduit 340 can be biodegradable or include one or more biodegradable portions. Biodegradation of conduit 340 can be stress or strain dependent biodegradation, or can depend on other physiological or artificially induced mechanical, chemical, or physical cues. Stress or strain dependent degradation (hereinafter "stress dependent degradation") kinetics of fiber matrix 320 can be customized for a desired remodeling of conduit 340, such as when conduit 340 is a harvested vessel such as a harvested saphenous vein graft. Stress based degradation or other physiologically or artificially induced mechanisms can be used such that degradation would occur, accelerate, and/or be triggered at a time when mechanical support would be no longer desired (this degradation arrangement could be relatively continuous or triggered by a threshold). In some embodiments, fiber matrix 320 is used to provide temporary mechanical support to a tissue based conduit 340 that is subjected to supra-physiologic conditions. The desired degradation mechanism would be constructed and arranged as follows. Device 300 is placed between a first body space, such as the aorta, and a second body space, such as a coronary artery. After this implantation, the initial levels of stress applied to fiber matrix 320 are at a maximum as the underlying conduit 340 (e.g. a harvested vessel) is not yet adapted (e.g. example walls have not yet thickened) and has minimum contribution toward stress relief. The initial degradation rate can be configured to be minimal at this initial stage. As the tissue begins to remodel constructively in response to the increased stress (e.g. vessel tissue training), the stress relief provided by flow conduit 340 will be increased, resulting in lesser stress transmission to fiber matrix 320. Fiber matrix 320 is constructed and arranged to trigger a mechanism by which the degradation of the material would be accelerated, and with increased degradation would follow increased tissue training, consequential increased degradation, and so on. A similar feedback approach can be applied when other physiologic mechanisms are used to control the degradation. Matrix 320 degradation can be artificially induced and imaging techniques can be used to externally monitor the progression of the graft remodeling. The degradation can be progressively triggered, such as by the intravenous administration of a drug.

In some embodiments, fiber matrix 320 is a matrix comprising a polymeric network possessing functional groups acting as part of a polymer backbone and/or as crosslinking molecules for the network. The functional groups are designed to dissociate from the polymer in the presence of naturally occurring enzymes in vivo. The functional groups also possess a receptor for a synthetic molecule (ligand) which is stored in microcapsules embedded at strategic locations, and with a specific distribution, within the matrix. The wall of the microcapsule has a permeability that is directly proportional to the level of stress or strain applied to the wall. A reaction is achieved where higher stress yields larger pores; larger pores yields higher permeability; and higher permeability yields higher release of ligands. In the presence of the synthetic ligands released by the microcapsules, the receptor of the functional group creates a steric hindrance for the naturally occurring enzymatic cleavage resulting in a reduced degradation rate.

In some embodiments, a fiber matrix 320 with stress based biodegradation surrounds a tissue based conduit 340 that is initially damaged but subjected to physiologic demands and therefore in need of temporary support while the healing process takes place. In some embodiments, a semi-permeable membrane surrounds a biodegradable fiber matrix 320, and the membrane pores expand under stress to increase biodegradation.

Fiber matrix 320 can be constructed and arranged to have stress based responses other than biodegradation, such as chemical, biological, or other responses. Alternative or additional to degradation based kinetics, fiber matrix 320 can achieve other response kinetics such as other mechanical response kinetics, electrical response kinetics, drug eluting kinetics, or another type of reaction kinetics. In some exemplary applications, graft device 300 can be sensitized to the local levels of oxygen tension that controls the kinetics of release of angiogenic factors such as VEGF. Initially, low oxygen tension yields high VEGF release; high VEGF release yields high angiogenesis; high angiogenesis yields higher oxygen tension which then cause lower release of VEGF.

Figure 3:
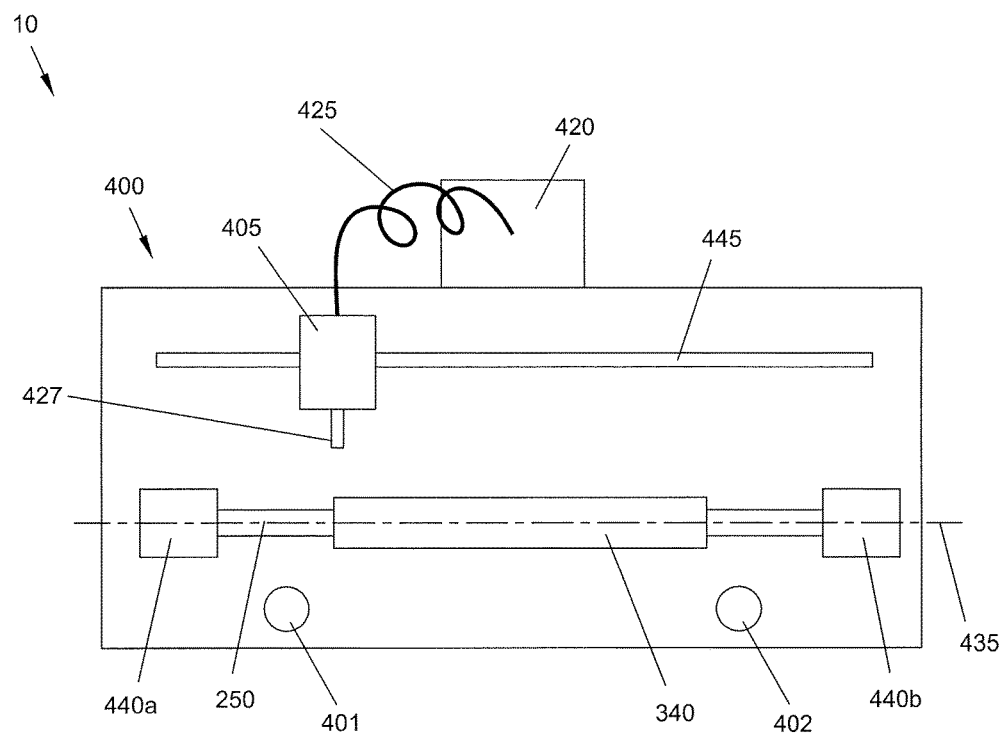
FIG. 3 illustrates a side view of an exemplary embodiment of an apparatus for applying a fiber matrix to a tubular member.
Figure 4:
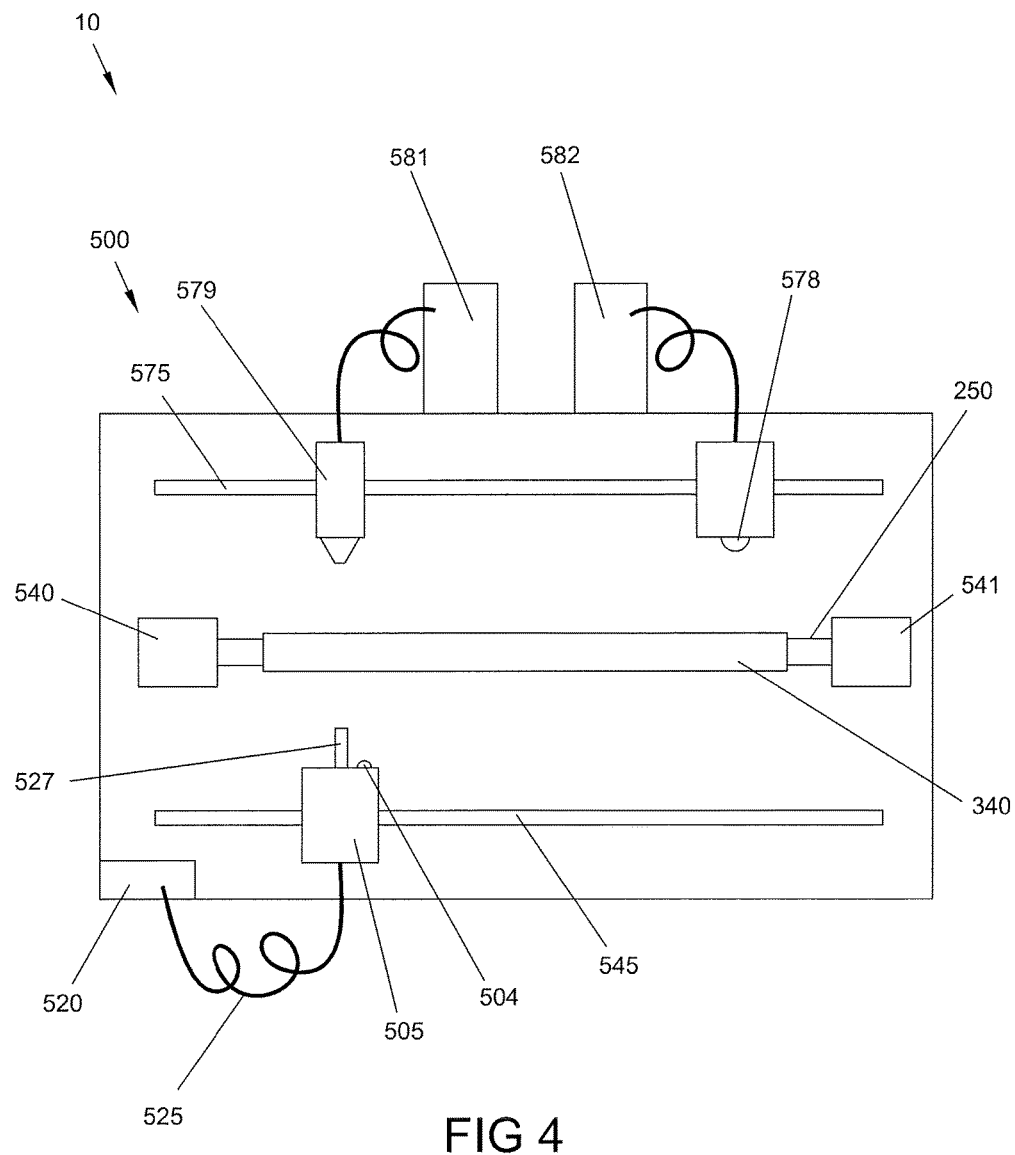
FIG. 4 illustrates a side view of another exemplary embodiment of an apparatus for applying a fiber matrix to a tubular member.

The apparatus of FIGS. 1, 3 and 4 can be used to apply the fiber matrix 320 around conduit 340 to produce graft device 300. The apparatus can be constructed and arranged, and settings established to produce particular graft device 300 properties. In some embodiments, graft device 300 properties are generated to achieve desired results when graft device 300 is implanted in a patient. Such graft device 300 properties include but are not limited to: thickness, elastic modulus, porosity, water permeability, compliance and suture retention strength. In some embodiments, fiber matrix 320 comprises a thickness greater than 100 μm, more typically between 150 μm and 220 μm. In some embodiments, graft device 300 has a relatively uniform thickness, with thickness deviations of less than 25%. In some embodiments, fiber matrix 320 is produced to provide a circumferential and longitudinal wall elastic tension between 0.8 N/cm and 1.6 N/cm. In some embodiments, the elastic modulus of the fiber matrix 320 is between 0.5 MPa and 1.5 MPa, and more preferably between 0.5 MPa and 1.0 MPa. Fiber matrix 320 porosity is preferably greater than 80%. Water permeability is preferably greater than 15 mL/min/cm2 at 120 mmHg. Compliance is preferably greater than $2 \times 10^{-4}$ mmHg-1 and less than $30 \times 10^{-4}$ mmHg-1, and more preferably between $10 \times 10^{-4}$ mmHg-1 and $20 \times 10^{-4}$ mmHg-1. In some embodiments, graft device 300 comprises one or more end portions with a fiber matrix configured to create an end portion with a suture retention strength greater than 100 gram force, and more preferably greater than 200 gram force.

Figure 3A:
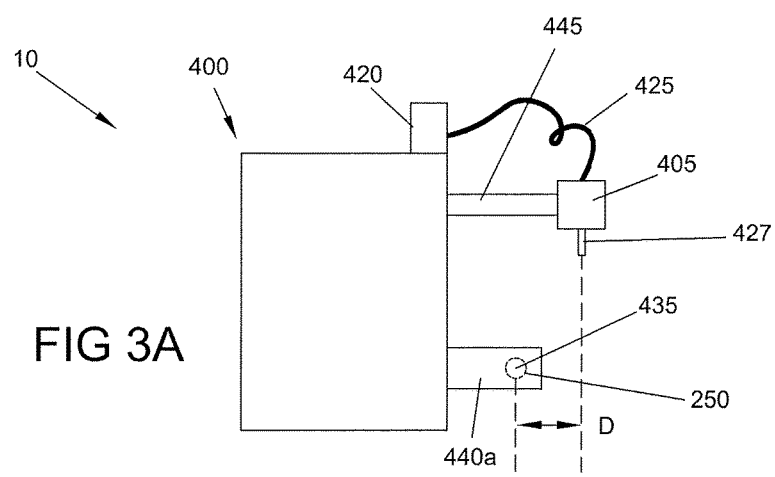
FIG. 3A illustrates an end view of the apparatus of FIG. 3.

Referring now to FIGS. 3 and 3A, side and end views, respectively, of another embodiment of an apparatus for producing a graft device is illustrated. Apparatus 10 includes electrospinning unit 400 and mandrel 250. A tubular member, conduit 340, has been placed around mandrel 250. Conduit 340 can comprise living tissue and/or artificial materials, as has been described in detail hereinabove. Electrospinning unit 400 includes nozzle assembly 405 including nozzle 427. Nozzle 427 can be constructed of stainless steel. In some embodiments, nozzle 427 has a tubular construction with a length of approximate 1.5", an ID of 0.047" and an OD of 0.065". In some embodiments, nozzle 427 has an ID between 0.047" and 0.055". The nozzle can be generally cylindrical and configured about a straight axis. Alternatively, the nozzle could be oval (not shown) or configured with multiple openings aligned along a straight line or otherwise (also not shown). The nozzle can include an insulating coating, with the tip of nozzle 427 exposed (e.g. non-insulated), such as with an exposed length of approximately 1 cm. Nozzle geometry and electrical potential voltages applied between nozzle 427 and mandrel 250 are chosen to control fiber generation. In some embodiments, fibers are created with a diameter between 0.1 μm and 2.0 μm, more typically with a diameter between 0.1 μm and 1.0 μm.

Mandrel 250 is positioned in a particular spaced relationship from nozzle assembly 405 and nozzle 427. For example, mandrel 250 can be positioned above (as shown) or below nozzle assembly 405. In some embodiments, mandrel 250 is located to the right or left of nozzle assembly 405. The distance between mandrel 250 and the tip of nozzle 427 is typically less than 20 cm, more typically less than 15 cm. In some embodiments, the tip of nozzle 427 is approximately 12.5 cm from mandrel 250. Alternatively, multiple nozzles (not shown), for example nozzles of similar or dissimilar configurations, can be positioned in various orientations relative to mandrel 250. Two or more of the multiple nozzles can each deliver one or more fibers to conduit 340 and/or mandrel 250 simultaneously, or sequentially.

An electrical potential can be applied between nozzle 427 and one or both of conduit 340 and mandrel 250. The electrical potential can draw at least one fiber from nozzle assembly 405 to conduit 340. Conduit 340 can act as the substrate for the electrospinning process, collecting the fibers that are drawn from nozzle assembly 405 by the electrical potential.

In some embodiments, mandrel 250 and/or conduit 340 has a lower voltage than nozzle 427 to create the electrical potential. For example, the voltage of mandrel 250 and/or conduit 340 can be a negative or zero voltage while the voltage of nozzle 427 can be a positive voltage. The fluid mandrel and/or conduit 340 can have a voltage of about −5 kV (e.g., −10 kV, −9 kV, −8 kV, −7 kV, −6 kV, −5 kV, −4.5 kV −4 kV, −3.5 kV, −3.0 kV, −2.5 kV, −2 kV, −1.5 kV, −1 kV) and the nozzle 105 can have a voltage of about +15 kV (e.g., 2.5 kV, 5 kV, 7.5 kV, 12 kV, 13.5 kV, 15 kV, 20 kV). In some embodiments, the potential difference between nozzle 427 and mandrel 250 and/or conduit 340 can be from about 5 kV to about 30 kV. This potential difference draws fibers from nozzle 427 to conduit 340. In some embodiments, nozzle 427 is placed at a potential of +15 kV while mandrel 250 is placed at a potential of −5 kV.

A polymer solution, stored in a sterile condition in polymer solution dispenser 420, can be delivered to nozzle assembly 405 through a polymer solution delivery tube 425. The electrical potential between nozzle 427 and conduit 340 and/or mandrel 250 can draw the polymer solution through nozzle 427 of nozzle assembly 405. Electrostatic repulsion, caused by the fluid becoming charged from the electrical potential, counteracts the surface tension of a stream of the polymer solution at nozzle 427 of nozzle assembly 405. After the stream of polymer solution is stretched to its critical point, one or more streams of polymer solution emerges from nozzle 427 of nozzle assembly 405, and/or at a location below nozzle assembly 405, and move toward the negatively charged conduit 340. Using a volatile solvent, the solution dries substantially during transit and the fiber is deposited on conduit 340.

Mandrel 250 is configured to rotate about an axis 435, with nozzle 427 perpendicular to axis 435. The rotation around axis 435 allows the fiber matrix to be deposited along all sides, or around the entire circumference of conduit 340. Mandrel 250 can be rotated by at least one motor 440a, 440b in direct or indirect communication with the ends of mandrel 250. In some embodiments, the electrospinning unit includes a single motor that rotates one end of mandrel 250. In some embodiments, two motors 440a, 440b are used. For example, motor 440a can be in communication with one end of mandrel 250 while motor 440b is in communication with the opposite end of mandrel 250. The rate of rotation of mandrel 250 can depend on how the fiber matrix needs to be applied to conduit 340. For example, for a thicker fiber matrix, the rotation rate can be slower than if a thinner fiber matrix is desired.

In addition to conduit 340 rotating around axis 435, nozzle assembly 405 can move, such as when driven by drive assembly 445 in a reciprocating or oscillating horizontal motion. Drive assembly 445 comprises a linear drive assembly, such as a belt driven drive assembly comprising two or more pulleys driven by one or more stepper motors. Additionally or alternatively, nozzle assembly 405 can be constructed and arranged to rotate around axis 435, rotating means not shown. Additionally or alternatively, mandrel 250 can be constructed and arranged to oscillate in an axial direction. The length of the drive assembly and the linear motion applied to nozzle assembly 405 can vary based on the length of the tubular member to which a fiber matrix will be delivered. For example, the supported linear motion of drive assembly 445 can be about 10 cm to about 50 cm. Nozzle assembly 405 can move along drive assembly 445 to apply a fiber matrix to the entire length, or specific portions of a length of a conduit 340. In some embodiments, fiber is applied to the entire length of conduit 340 plus an additional 5 cm (to mandrel 250) on either end of conduit 340. In some embodiments, fiber is applied to the entire length of conduit 340 plus at least 1 cm beyond either end of conduit 340.

Nozzle assembly 405 can be controlled such that specific portions along the length of the conduit 340 are reinforced with a greater amount of fiber matrix as compared to other or remaining portions. In addition, conduit 340 can be rotating around axis 435 while nozzle assembly 405 is moving along drive assembly 445 to provide control over the location on conduit 340 where the fiber matrix will be applied. In some embodiments, nozzle assembly 405 is translated back and forth at a velocity of approximately 200 mm/sec. Rotational speeds of mandrel 250 and translational speeds of nozzle 427 can be relatively constant, or can be variable.

Apparatus 10 can also include a power supply, not shown but configured to provide the electric potentials to nozzle 427 and mandrel 250, as well as supply power to other components of apparatus 10. The power supply can be connected, either directly or indirectly, to at least one of mandrel 250 or conduit 340. Power can be transferred from the power supply to mandrel 250 and/or conduit 340 by, for example, a wire.

Apparatus 10 can also include inlet port 401 and/or outlet port 402. Ports 401 and 402 can be used to control the environment surrounding nozzle 427 and/or mandrel 250. Ports 401 and/or 402 can be configured to be both an inlet port and an outlet port. Apparatus 10 can include a housing, not shown but typically attachable to electrospinning unit 400 and defining a chamber surrounding nozzle 427 and/or mandrel 250, such that ports 401 and 402 can control a more limited (smaller) environment surrounding nozzle 427 and/or mandrel 250. Ports 401 and 402 can be used to introduce or remove one or more gases, introduce or remove humidity, control temperature, maintain or control sterility; and provide other environmental controls as described in reference to FIG. 1 hereabove.

Referring specifically to FIG. 3A, the distal end of nozzle 427 is positioned vertically offset a distance "D" from the axis 435 of mandrel 250. Typically offsets are chosen between 1.0 cm and 5.0 cm and prevent any polymer solution or other material that falls from nozzle 427, due to gravity or another force, from undesirably landing on mandrel 250 and/or conduit 340.

Referring now to FIG. 4, a side view of another embodiment of an apparatus for producing a graft device is illustrated. Apparatus 10 includes electrospinning unit 500 and mandrel 250. A tubular member, conduit 340, has been placed around mandrel 250. Conduit 340 can comprise living tissue and/or artificial materials, as has been described in detail hereabove. Electrospinning unit 500 includes nozzle assembly 505 including nozzle 527. Nozzle 527 can comprise a single tube construction, similar to nozzle 427 of FIG. 3. Nozzle 527 can include multiple output ports, such as multiple output configurations including but not limited to: side by side outlet ports in a single housing such as two lumens in a single tube, two or more coaxial nozzles, and the like.

Mandrel 250 is positioned above nozzle assembly 505 such that polymer solution or other material falling off of nozzle assembly 505 avoids landing on mandrel 250 and/or conduit 340. An electrical potential can be applied between nozzle 527 and one or both of conduit 340 and mandrel 250. The electrical potential can draw at least one fiber from nozzle assembly 505 to conduit 340, as has been described in detail hereabove. Conduit 340 can act as the substrate for the electrospinning process, collecting the fibers that are drawn from nozzle assembly 505 by the electrical potential.

A polymer solution, stored in polymer solution dispenser 520, can be delivered to nozzle assembly 505 through polymer solution delivery tube 525. The electrical potential between nozzle 527 and conduit 340 and/or mandrel 250 can draw the polymer solution through nozzle 527 of nozzle assembly 505 as described in detail hereabove. Using a volatile solvent, the solution dries substantially during transit and the fiber is deposited on conduit 340.

Mandrel 250 is positioned horizontally and configured to rotate with nozzle 527 oriented relatively perpendicular to mandrel 250. Mandrel 250 can be rotated by motor 540, connected to one end of mandrel 250. The opposite end of mandrel 250 is attached to bearing 541, configured to allow free rotation of mandrel 250 as driven by motor 540. Nozzle assembly 505 can move along drive assembly 545, such as in a reciprocating or oscillating motion described in detail hereabove in reference to drive assembly 445 of FIG. 3. In some embodiments, nozzle assembly 505 is translated back and forth at a velocity between 100 and 300 mm/sec, typically approximately 200 mm/sec.

Apparatus 10 can also include a power supply (not shown). The power supply can be connected, either directly or indirectly, to at least one of mandrel 250 or conduit 340. Power can be transferred from the power supply to mandrel 250 and/or conduit 340 by, for example, a wire. The power supplied to mandrel 250 and/or conduit 340 can provide the potential difference between nozzle 427 and conduit 340.

Electrospinning unit 500 can include an optical imaging device, such as a laser micrometer and/or an optical imaging device including camera 504 positioned on nozzle assembly 505. Camera 504 and image processing functions included in electrospinning unit 500 or another component of apparatus 10 can be used to visually measure and/or identify features of mandrel 250, conduit 340, and/or the fiber matrix electrospun about conduit 340. In some embodiments, camera 504 is used to measure the cross sectional profile (e.g. local thickness) of conduit 340 and/or the electrospun fiber matrix. In some embodiments, camera 504 and/or another imaging or measurement apparatus such as a laser micrometer, not shown, is used to identify one or more sidebranch locations, such as when conduit 340 is a harvested vessel such as a harvested saphenous vein graft with ligated sidebranches. Measurement and feature identification of camera 504 can be used to adjust one or more electrospinning parameters, including but not limited to: amount of fiber deposited at a location, polymer solution flow rate; fiber diameter; fiber wetness; and combinations of these. Alternatively or additionally, camera 504 can be mounted at another location on electrospinning unit 500.

Electrospinning unit 500 further includes a second translational drive assembly, drive assembly 575, of similar or dissimilar construction to drive assembly 545. Mounted to drive assembly 575 are laser 578 and agent delivery assembly 579. Drive assembly 575 can be configured to translate agent delivery assembly 579 and laser 578 independently or in synchrony. Agent delivery assembly 579 can include one or more pumping mechanisms and a nozzle, such as to spray one or more drugs or other agents onto mandrel 250, conduit 340, or the fiber matrix applied to conduit 340. The agents can be delivered prior to electrospinning, during electrospinning, and/or after electrospinning is complete.

In some embodiments, electrospinning unit 500 is further configured to apply an intermediate layer between conduit 340 and the restrictive fiber matrix. Agent delivery assembly 579 can deliver the intermediate layer prior to beginning the electrospinning process. For example, the intermediate layer can comprise an adhesive layer or a chemical treatment to promote adhesion between conduit 340 and the fiber matrix, such as an adhesive layer comprising fibrin glue that has been delivered through agent delivery assembly 579. In some embodiments, the intermediate layer can comprise a protective layer which can be configured to provide mechanical protection, chemical protection, or both. Additionally, the protective layer can protect conduit 340 during the application of the restrictive fiber matrix. In some embodiments, the intermediate layer can be selected from the group consisting of: a nutrient providing layer; a compressible layer; a non-compressible layer; an elastic layer; a viscoelastic layer; a viscous layer; a layer to control vein compliance, a layer to control wall thickness, and combinations of these. Agent delivery assembly 579 can be constructed and arranged to deliver materials within the fiber matrix, between the fiber matrix and conduit 340, and external to the fiber matrix. Agent delivery assembly 579 can deliver materials prior to, during, or after application of the fiber matrix.

Pharmaceutical drugs or other agents can be included in a polymer solution that is used to electrospin a fiber matrix onto a conduit 340. However, the electrospinning process can be harsh and can result in the degradation of the drug or agent. Therefore, in some embodiments, the pharmaceutical drug or other agent is applied via a separate source, such as agent delivery assembly 579. Examples of drugs that can be introduced include, without limitation, time release drugs; anti-clotting drugs (e.g., heparin, aspirin and clopidogrel); vasoactive drugs and molecules such as nitric oxide ("NO"), carbon monoxide ("CO"), papaverine, norepinephrine and sodium nitroprusside; antibiotics; anti-proliferative agents; or analgesics or anesthetics (e.g. acetaminophen, naproxen, ibuprofen, lidocaine), any or all of which can be stored in agent dispenser 581. In some embodiments, cells (from autogenous or allogeneic sources) such as endothelial cells, smooth muscle cells, myofibroblasts, mesenchymal stem cells, endothelial progenitor cells, hematopoietic stem cells, bone marrow-derived progenitor cells, other adult stem cells, or embryonic stem cells are included in the agent. When the conduit is a living tissue, cell treatment can help replenish the various cellular constituents of the tissue, or repair or remodel the tissue. The delivery of either stem cells, or fully differentiated adult cells via the fluid source, can provide biological support to the conduit. Specifically, in the case of a saphenous vein graft, the delivered cells could be endothelial cells or endothelial progenitor cells that will populate the graft lumen in areas of native endothelial cell denudation. When conduit 340 is a non-living tissue or material, inclusion of cells (e.g., cell seeding) can provide functionalization to the material such as antithrombogenicity and/or the cells can provide a chemotactic component for cell repopulation once implanted in vivo. In some embodiments, an agent configured to adjust biodegradation of the fiber matrix, such as to speed up or slow down the degradation, is delivered by agent delivery assembly 579. In some embodiments, agent delivery assembly 579 delivers an agent comprising one or more drugs or other agents encapsulated in microspheres. In some embodiments, an agent configured to protect conduit 340 from one or more solvents is delivered by agent delivery assembly 579.

Agent delivery assembly 579 can apply a mist to conduit 340, such as a mist applied through an atomizing or other nozzle of agent delivery assembly 579 prior to beginning the electrospinning process. In some embodiments, a mist solution can be applied for a time period less than one minute, typically approximately 5-10 seconds. The mist can include one or more agents, such as agents selected from the group consisting of: hydrating agents; dehydrating agents; nutrient agents; antimicrobial agents; vasorelaxing agents such as papaverine; vasoconstricting agents such as norepinephrine; and combinations of these. The mist solution can have a pH associated with the patient's physiology. Alternatively or additionally, the mist can be applied during the electrospinning process. In some embodiments, the mist can be applied while the fibers are being delivered, or during a period in which the fiber deposition is temporarily halted. In some embodiments, an external sprayer, such as a hand-held sprayer, is used to apply the mist. Potential benefits of the mist application include but are not limited to: maintenance of conduit 340 in a properly hydrated state; inclusion of metabolites in the graft device; contamination reduction; sterility improvement; relaxation of smooth muscle cells such as to reduce trauma to conduit 340; buffering of conduit 340 against changes in pH induced by a polymer, solvent, or other polymer solution component; and combinations of these.

Alternatively or additionally, agent delivery assembly 579 can deliver an imaging agent used in post-implant imaging. For example, agent delivery assembly 579 can deliver a radiopaque substance such as barium sulfate used to identify the graft device in an X-ray. Alternatively or additionally, agent delivery assembly 579 can deliver a magnetic or paramagnetic material such as a material used to identify the graft device in an MRI image or to evaluate mechanical properties (e.g., compliance) such as via a heart-gated imaging technique in combination with live pressure/flow measurements. In some embodiments, agent delivery assembly 579 is configured to deliver a fluorescent agent, such as an agent configured to be visualized by a imaging device of apparatus 10, such as an imaging device configured to visualize fiber delivery pathways. The imaging agent can be delivered prior to, during, and/or subsequent to the delivery of the fibers comprising the restrictive fiber matrix.

Laser 578, via energy source 582, can be configured to modify mandrel 250, conduit 340 and/or the fiber matrix applied to conduit 340. Modification can include removal of material. Alternatively or additionally, modification can include creating one or more marks or other visible characteristics, such as a marking applied to the fiber matrix which is indicative of valve direction when conduit 340 comprises a vein graft including one or more venous valves.

A tubular member comprising a harvested vessel, e.g. a saphenous vein, can comprise side branches which are ligated prior to the electrospinning process. In some embodiments, electrospinning unit 500 is configured to modify the application of the fiber matrix proximate the ostium of the sidebranch. For example, electrospinning unit 500 can apply more fiber at a sidebranch location. Alternatively or additionally, nozzle 527 can retract to increase the distance between nozzle 527 and conduit 340 as it approaches a sidebranch location, such as a sidebranch location identified by camera 504 as has been described hereabove. Agent delivery assembly 579 can apply one or more agents at a sidebranch location. Laser 578 can apply energy to a sidebranch location, such as to remove tissue or deposited fiber.

Figure 5:
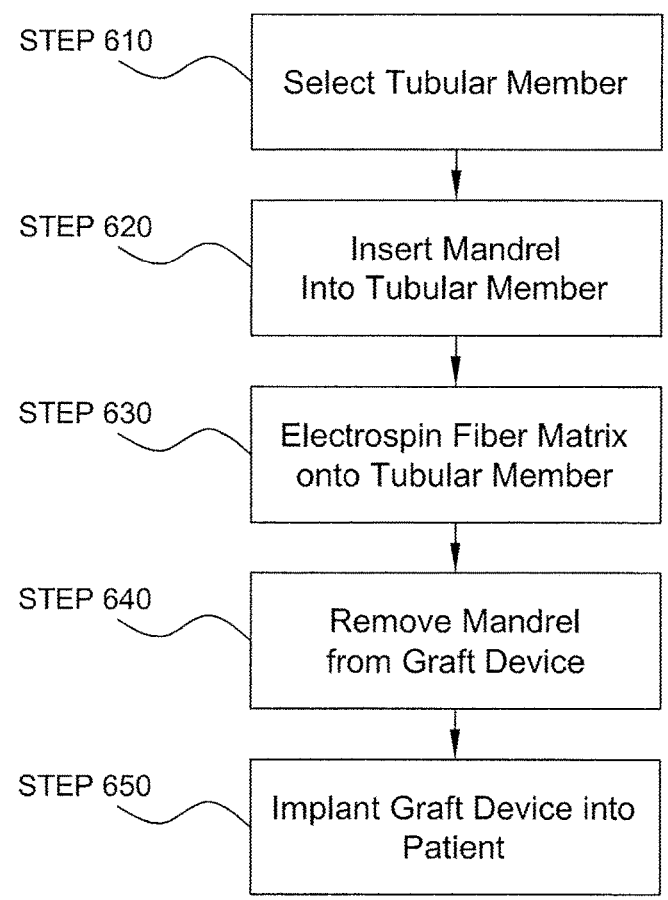
FIG. 5 illustrates a flow chart of an example method of creating a graft device by applying a fiber matrix to a tubular member.

Referring now to FIG. 5, a flow chart of a method of creating a graft device is illustrated. In STEP 610, a tubular member is chosen and size to the desired length, such as a tubular member comprising living tissue and/or artificial materials. In some embodiments, the tubular member is a segment of saphenous vein harvested from a patient, such as a saphenous vein harvested from the patient selected to receive the graft device in a coronary bypass procedure.

In STEP 620, the tubular member can be placed over a mandrel. The mandrel and tubular member can then be placed into an electrospinning unit, such as the mandrel and electrospinning units described hereabove in reference to FIGS. 1, 3 and 4. The mandrel and tubular member can first be placed into a cartridge, such as a disposable cartridge operably received by an electrospinning unit. The cartridge can create a chamber, such as an environmentally controlled chamber configured to support the application of the fiber matrix in the electrospinning process. The mandrel can be positioned horizontally or vertically, with one or more nozzles positioned above, below and/or to the side of the mandrel.

In STEP 630, a fiber matrix is delivered to the tubular member creating the graft device. Prior to or during the delivery of the fibers to the tubular member, one or more process parameters or other input data can be input into the electrospinning unit, such as via a user interface such as the user interface 150 of FIG. 1. Alternatively or additionally, one or more input data can be entered automatically, such as via a barcode or other information logging means integral to a mandrel, cartridge, or other apparatus component. Typical data input includes but is not limited to: mandrel geometry data such as mandrel outer diameter (OD); tubular member data such as tubular member length or outer diameter; patient data such as patient physiologic data; environmental data such as temperature and/or humidity data; and combinations of these.

Prior to delivery of the fiber matrix, a mixing step can be performed to mix one or more components of the polymer solution to be delivered through a nozzle. Alternatively or additionally, a filtering step, such as to pass through polymer solution through a 0.2 μm filter, can be performed to remove undesired particulate or other undesired material and/or to sterilize the polymer solution.

The fiber matrix delivery can be delivered through one or more nozzles, such as the nozzles described in reference to FIGS. 1, 3 and 4 hereabove. A delivery nozzle can be mounted to a linear drive assembly configured to oscillate the nozzle back and forth along at least the entire length of the tubular member, such as at a rate between 100 mm/sec and 300 mm/sec, typically approximately 200 mm/sec. In some embodiments, the nozzle translates an additional 1 cm, typically 5 cm, beyond each end of the tubular member. In some embodiments, the nozzle translates at least 50% of the length of the mandrel, such as when the mandrel is placed in a cartridge with a length approximating the length of the mandrel.

With the mandrel and tubular member rotating, and the nozzle oscillating back and forth, the fiber matrix is applied. One or more environmental conditions can be maintained and/or assured by the electrospinning unit or other apparatus components. In some embodiments, the electrospinning unit includes environmental control components such as heaters, coolers, humidifiers, dehumidifiers, ventilators, and the like, to maintain and/or control the environment in a cartridge, or other relatively closed area surrounding the tubular member, during delivery of the fiber matrix.

Numerous process parameters are used to configured the structure and other characteristics of the fiber matrix, these process parameters including but not limited to: electric potential at a nozzle; electric potential at the tubular member and/or mandrel; mandrel rotation speed and direction; nozzle translation speed; distance of nozzle to mandrel; polymer solution composition including polymer types, solvent types and relative concentrations; and combinations of these. The electrospinning process can be performed maintaining one or more process parameters relatively constant. Alternatively, the process parameters can be varied such as to vary based on one or more factors. These process varying factors include but are not limited to: a temporal value such as time elapsed since fiber delivery initiation; position of nozzle relative to tubular member such as position relative to a sidebranch or an end of the tubular member; current thickness of fiber matrix in the application process such as a factor that changes near the beginning of the fiber application or near the completion of the fiber application; environmental condition such as temperature or humidity value; and combinations of these. In some embodiments, the direction of mandrel rotation is changed after initiation of fiber delivery.

In STEP 640, the mandrel can be removed from the graft device. Removal of the graft device from the mandrel can involve the step of cutting fiber matrix between the tubular member and the mandrel, such as with cutting tool 170 of FIG. 1, and/or to remove fiber matrix that extends beyond one or more ends of the tubular member.

In STEP 650, the graft device is implanted in the patient, such as to create a fluid connection between the aorta and an occluded coronary artery of the patient. One end of the graft device can be anastomosed to a source of oxygenated blood, such as to an artery such as the aorta. The other end of the graft device is anastomosed to a part of the vasculature with limited or no oxygenated blood, such as at a vessel location distal to a full or partial occlusion.

One or more additional processes can be performed in the creation of the graft device. These additional processes can be performed prior to delivery of the fiber matrix, during delivery of the fiber matrix, and/or after the fiber matrix is in place. Such additional processes include but are not limited to: application of one or more agents such as by agent delivery assembly 579 of FIG. 4; application of a mist; application of energy such as cryogenic or other cooling energy, heat; UV irradiation; radiofrequency energy; microwave energy; ultrasound energy; or laser energy such as laser energy delivered by laser 578 of FIG. 4; processing to create a chemical change to the graft device; processing to create a mechanical change to the graft device; and processing to create a geometric change to the graft device. In some embodiments, additional processing is performed at a graft device location proximate a sidebranch. In some embodiments, the tubular member is maintained at a temperature below room temperature (e.g. to approximately 4° C.), such as a harvested vein graft maintained at a temperature cool enough to reduce physiologic changes.

A patient image can be obtained in the process of creating the graft device. The image can be obtained prior to vessel harvesting, such as to identify a portion of one or more particular vessels to be harvested, such as to secure a vessel with a particular geometry and/or to avoid one or more sidebranches. The obtained patient image can be used to select one or more anastomotic sites to be used in placement of the graft device in a bypass procedure such as a coronary bypass procedure. The patient image can be used in mandrel selection, such as to select a mandrel with a particular two or three dimensional shape, length, or outer diameter. The patient image can be used in setting one or more electrospinning parameters, such as fiber matrix thickness; delivery pattern; and polymer solution composition.

A graft device diagnostic procedure can be performed in the process of creating the graft device, such as a process performed on the mandrel, the tubular member or a partially or fully applied fiber matrix. Measurement or visual identification procedures can be performed such as with camera 504 of FIG. 4. In some embodiments, a measurement procedure is performed and one or more electrospinning parameters are set based on the measurement procedure. In some embodiments, a measurement procedure is performed and one or more additional processes are performed, such as a process including delivery of an agent such as by agent delivery assembly 579 of FIG. 4, or a process including delivery of energy such as by laser 578 of FIG. 4.

A patient diagnostic procedure can be performed in the process of creating the graft device. In some embodiments, the patient diagnostic includes gathering patient physiologic data such as patient diastolic and systolic blood pressure readings used to set one or more electrospinning parameters such as fiber matrix thickness; delivery pattern; and polymer solution composition.

Figure 6:
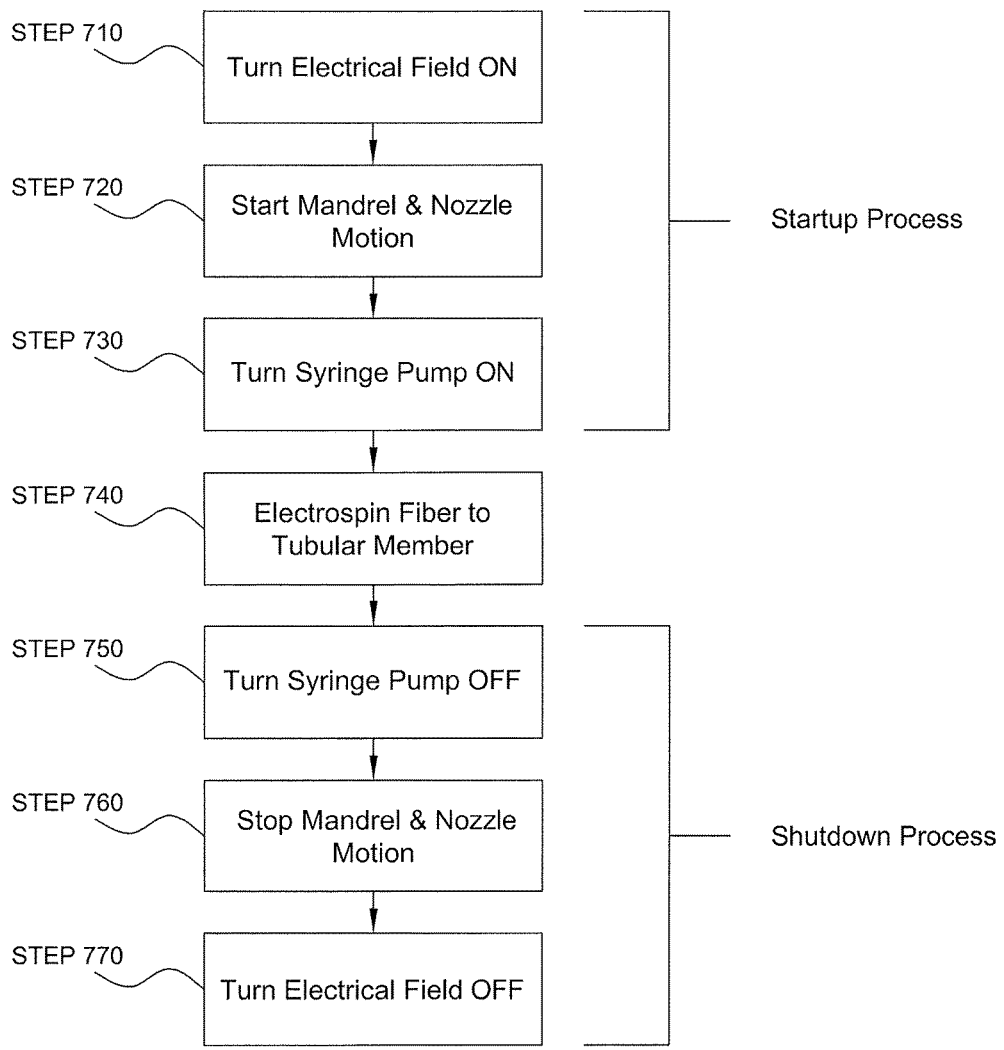
FIG. 6 illustrates a flow chart of an example method of initiating the delivery of a fiber matrix to a tubular member.

Referring now to FIG. 6, a flow chart of a method of initiating deliver of fiber to a tubular member is illustrated. A mandrel is inserted into an electrospinning unit as has been described in reference to FIG. 5 hereabove. A sequence of steps is used to prevent an undesired initial application of fiber to the tubular member, such as an initial application of an excess of fiber over a small area.

In STEP 710, an electric field is applied between at least one nozzle and the mandrel and/or tubular member. In some embodiments, electric potentials applied are +15 kV to a nozzle and −5 kV to the mandrel.

Subsequently, in STEP 720, the mandrel and tubular member rotation is initiated. Nozzle motion (e.g. translation back and forth along the mandrel) can be initiated as well.

Subsequently, in STEP 730, a syringe pump configured to deliver polymer solution to the nozzle is activated to begin pumping and delivery of one or more fibers from one or more nozzles.

In STEP 740, the fiber delivery to the tubular member continues.

When it is desired to cease fiber delivery, such as at the end of the fiber delivery process, when an alarm or alert condition is entered, when a pre-determined diagnostic step is to be performed, or at another time, a preferred sequence of steps are performed beginning with STEP 750 in which the syringe pump polymer solution delivery is halted.

Subsequently, in STEP 760, mandrel rotation is halted. Nozzle translation can be halted as well.

Subsequently, in STEP 770, the electric field between at least one nozzle and the mandrel and/or tubular member is turned off.

In one embodiment, STEP 720 is performed before STEP 710. In another embodiment, STEP 770 is performed before STEP 760.

The electrospinning chambers and/or cartridge housings can assume numerous geometries, such as a tubular housings, rectangular housings, and trapezoidal housings. The housings can include multiple portions, such as upper and lower portions, and can include components such as hinges, doors, slots and other openings. In some embodiments, the housing comprises a semi-rigid plastic pouch with an opening. Cartridges can include one or more sensors or transducers. In some embodiments, one or more nozzles are integral to the cartridge, such as at a side or bottom location to prevent gravitational dripping of any substance from the nozzle onto the conduit. Alternatively or additionally, one or more nozzles can be integral to the electrospinning unit of the apparatus, similarly placed at any location into the cartridge, such as though a slot or door. While the conduit holder has been described in detail as a rotatable mandrel, other conduit holders can be employed, rotating and fixed, such as to accommodate other forms of tissue such as nerve tissue, tendon tissue, muscle tissue, ligament tissue, organ and other non-linear tissues, and other tissues.

While certain embodiments of the devices and methods have been described in reference to the environment in which they were developed, they are merely illustrative of the principles described herein. Modification or combinations of the above-described assemblies, other embodiments, configurations, and methods for carrying out the principles described herein, and variations of aspects of the principles described herein that are obvious to those of skill in the art are intended to be within the scope of the claims. In addition, where this application has listed the steps of a method or procedure in a specific order, it can be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. An electrospinning apparatus for applying an electrospun restrictive fiber matrix to a tubular member to create a graft device, the electrospinning apparatus comprising:
   a rotating assembly that rotates the tubular member;
   a polymer delivery assembly that delivers the electrospun restrictive fiber matrix to the tubular member;
   an imaging or measurement apparatus for identifying a side branch location of the tubular member;
   a controller that controls the polymer delivery assembly, the imaging or measurement apparatus, and the rotating assembly;
   a chamber comprising a chamber volume that surrounds the tubular member; and
   an environmental control assembly that exchanges gas within the chamber volume.

2. The electrospinning apparatus of claim 1, wherein the environmental control assembly is attachable to one or more ports of the chamber.

3. The electrospinning apparatus of claim 1, wherein the chamber comprises a disposable cartridge.

4. The electrospinning apparatus of claim 1, wherein the chamber comprises a sterility barrier between an internal chamber and an exterior surface.

5. The electrospinning apparatus of claim 1, further comprising at least one nozzle, and wherein the chamber surrounds the tubular member and the at least one nozzle.

6. The electrospinning apparatus of claim 1, wherein the chamber comprises one or more sensors.

7. The electrospinning apparatus of claim 1, wherein the chamber comprises an interior surface and an insulating layer positioned on the interior surface.

8. The electrospinning apparatus of claim 1, wherein the environmental control assembly exchanges gas within the chamber volume within a time period of no more than 2 minutes.

9. The electrospinning apparatus of claim 8, wherein the environmental control assembly exchanges gas within the chamber volume within a time period of no more than 1 minute.

10. The electrospinning apparatus of claim 1, wherein the environmental control assembly comprises a ventilation fan.

11. The electrospinning apparatus of claim 1, wherein the environmental control assembly is configured to control at least one of pressure, temperature, or humidity proximate the tubular member.

12. The electrospinning apparatus of claim 1, wherein the environmental control assembly is configured to control at least one of pressure, temperature, or humidity within the chamber volume.

13. The electrospinning apparatus of claim 1, wherein the environmental control assembly is configured to control a temperature proximate the tubular member between about 18° Celsius (C) and about 22° C.

14. The electrospinning apparatus of claim 1, wherein the environmental control assembly is configured to control a relative humidity proximate the tubular member between about 25% and about 50%.

15. The electrospinning apparatus of claim 1, wherein the chamber volume comprises a volume less than 140 liters.

16. The electrospinning apparatus of claim 1, wherein the controller comprises a graphical user interface comprising at least one user input component.

17. The electrospinning apparatus of claim 16, wherein the at least one user input component is configured to receive data selected from the group consisting of: a mandrel size, a nozzle speed, a polymer solution flow rate, a process time, and combinations thereof.

18. The electrospinning apparatus of claim 1, wherein the controller is configured to control a function selected from the group consisting of: rotating one or more mandrels; translating one or more nozzles; translating one or more mandrels; rotating one or more nozzles; monitoring an environment of an area surrounding the tubular member; maintaining an environment of an area surrounding the tubular member; maintaining pressure; maintaining temperature; maintaining humidity; applying an electrical potential between at least one nozzle and at least one mandrel; and combinations thereof.

19. The electrospinning apparatus of claim 1, further comprising a polymer solution supplied to the polymer delivery assembly to produce the electrospun restrictive fiber matrix, wherein the controller is configured to control a flow rate of the polymer solution.

20. The electrospinning apparatus of claim 1, wherein the rotating assembly comprises a mandrel that is slidingly received by the tubular member prior to the polymer delivery assembly delivering the electrospun restrictive fiber matrix to the tubular member.

21. The electrospinning apparatus of claim 20, wherein the electrospinning apparatus is configured to automatically detect a size of the mandrel.

22. The electrospinning apparatus of claim 21, wherein the electrospinning apparatus is further configured to adjust the delivery of the electrospun restrictive fiber matrix to the tubular member based on the size of the mandrel.

23. The electrospinning apparatus of claim 1, wherein the polymer delivery assembly comprises a nozzle.

24. The electrospinning apparatus of claim 23, wherein the tubular member comprises a first end and a second end, and wherein the nozzle travels a distance of about 5 centimeters (cm) past the first end and travels a distance of about 5 cm past the second end.

25. The electrospinning apparatus of claim 1, further comprising an agent delivery assembly that delivers an agent.

26. The electrospinning apparatus of claim 25, wherein the agent delivery assembly delivers the agent between the electrospun restrictive fiber matrix and the tubular member.

27. The electrospinning apparatus of claim 25, wherein the agent comprises a drug.

28. The electrospinning apparatus of claim 27, wherein the drug is selected from the group consisting of: a time release drug; an anti-clotting drug; heparin; aspirin; clopidogrel; a vasoactive drug; a vasoactive molecule; nitric oxide; carbon monoxide; papaverine; norepinephrine; sodium nitroprusside; an antibiotic; an anti-proliferative agent; an analgesic; acetaminophen; naproxen; ibuprofen; and combinations thereof.

29. The electrospinning apparatus of claim 1, further comprising an emergency shutoff.

30. The electrospinning apparatus of claim 29, wherein the emergency shutoff is configured to be automatically activated.

31. The electrospinning apparatus of claim 30, wherein the emergency shutoff is configured to be automatically activated by one or more of: a process parameter out of an expected value range; loss of power; a temperature or a humidity out of an accepted value range; a presence of fiber at an unacceptable location; a lack of sufficient flow of a polymer solution to a nozzle; a nozzle voltage at an unacceptable level; a mandrel voltage at an unacceptable level; a displacement of an internal component; and combinations thereof.

32. The electrospinning apparatus of claim 1, wherein the tubular member comprises living tissue selected from the group consisting of: vein; artery; lymphatic duct; vas deferens; tear duct; intestine; esophagus; ureter; urethra; trachea; bronchi; duct tissue; Eustachian tube; fallopian tube; and combinations thereof.

33. The electrospinning apparatus of claim 1, wherein the controller is configured to modify one or more parameters of the electrospinning apparatus based on an image obtained from the imaging or measurement apparatus.

34. The electrospinning apparatus of claim 1, wherein the controller is configured to modify one or more electrospinning parameters based on one or more measurements obtained by the imaging or measurement apparatus.

35. The electrospinning apparatus of claim 34, wherein the one or more electrospinning parameters comprises a distance between a nozzle and the tubular member.

36. The electrospinning apparatus of claim 34, wherein the one or more electrospinning parameters comprises a flow rate.

37. The electrospinning apparatus of claim 1, wherein the tubular member comprises a plurality of side branch locations.

38. The electrospinning apparatus of claim 1, wherein the imaging or measurement apparatus comprises a camera.

39. The electrospinning apparatus of claim 1, wherein the imaging or measurement apparatus comprises a laser micrometer.

40. The electrospinning apparatus of claim 1, wherein the electrospinning apparatus is configured to modify an application of the electrospun restrictive fiber matrix proximal to the side branch location.

* * * * *